US012736521B2

(12) United States Patent
Yang et al.

(10) Patent No.: US 12,736,521 B2
(45) Date of Patent: Sep. 15, 2026

(54) CURRENT AND RESISTANCE SENSOR

(71) Applicant: National Taiwan University, Taipei (TW)

(72) Inventors: Chii-Shen Yang, Taipei (TW); Yu-Hung Chen, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 249 days.

(21) Appl. No.: 18/335,688

(22) Filed: Jun. 15, 2023

(65) Prior Publication Data

US 2024/0230620 A1 Jul. 11, 2024

(30) Foreign Application Priority Data

Jan. 9, 2023 (TW) ................................ 112100886

(51) Int. Cl.
*G01N 33/487* (2006.01)
*G01N 33/58* (2006.01)
*G01N 33/68* (2006.01)

(52) U.S. Cl.
CPC ..... *G01N 33/48721* (2013.01); *G01N 33/583* (2013.01); *G01N 33/6848* (2013.01)

(58) Field of Classification Search
None
See application file for complete search history.

(56) References Cited

FOREIGN PATENT DOCUMENTS

WO WO 2018/073583 A1 4/2018
WO WO 2021/022360 A1 2/2021

OTHER PUBLICATIONS

T. Kaji, et al., "Enhanced Photocurrent Generation from Bacteriorhodopsin Photocells Using Grating-Structure Transparent Conductive Oxide Electrodes", Journal of Nanoscience and Nanotechnology, 16(4): p. 3206-3212, Apr. 2016.*
T. Yamada, et al., "Orientation of a Dip-Coated Bacteriorhodopsin Thin Film Studied by Second Harmonic Generation Interferometry", Japanese Journal of Applied Physics, 52, paper 05DB03, 5 pages, May 2013.*

* cited by examiner

*Primary Examiner* — J. Christopher Ball
(74) *Attorney, Agent, or Firm* — MUNCY, GEISSLER, OLDS & LOWE, P.C.

(57) ABSTRACT

A current and resistance sensor includes a photo-induced-voltage-generating solution chamber for receiving a photo-receptor-protein-containing solution; and a compound layer on one side of the photo-induced-voltage-generating solution chamber. The compound layer is responsive to changes in the amount of protons in the solution, and the compound layer is provided with a gap that is an electrically insulating discontinuity aligned with and spanning the photo-induced-voltage-generating solution chamber, such that the compound layer is divided into electrically independent portions, and changes in the amount of protons in the solution result in a detectable change in electrical current and/or resistance measured between the electrically independent portions across the gap.

14 Claims, 31 Drawing Sheets

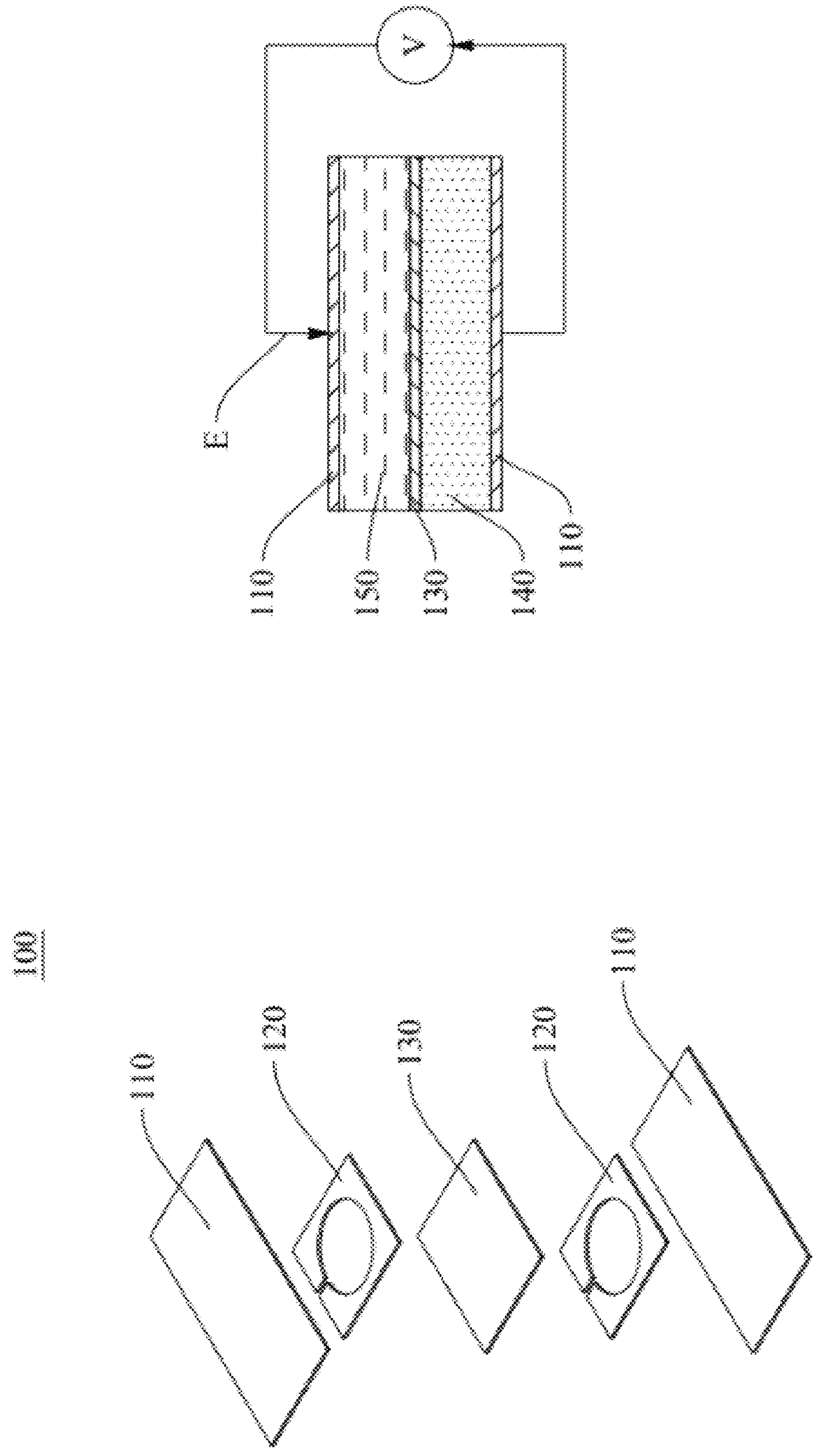
(B)
(A)
【FIG. 1】

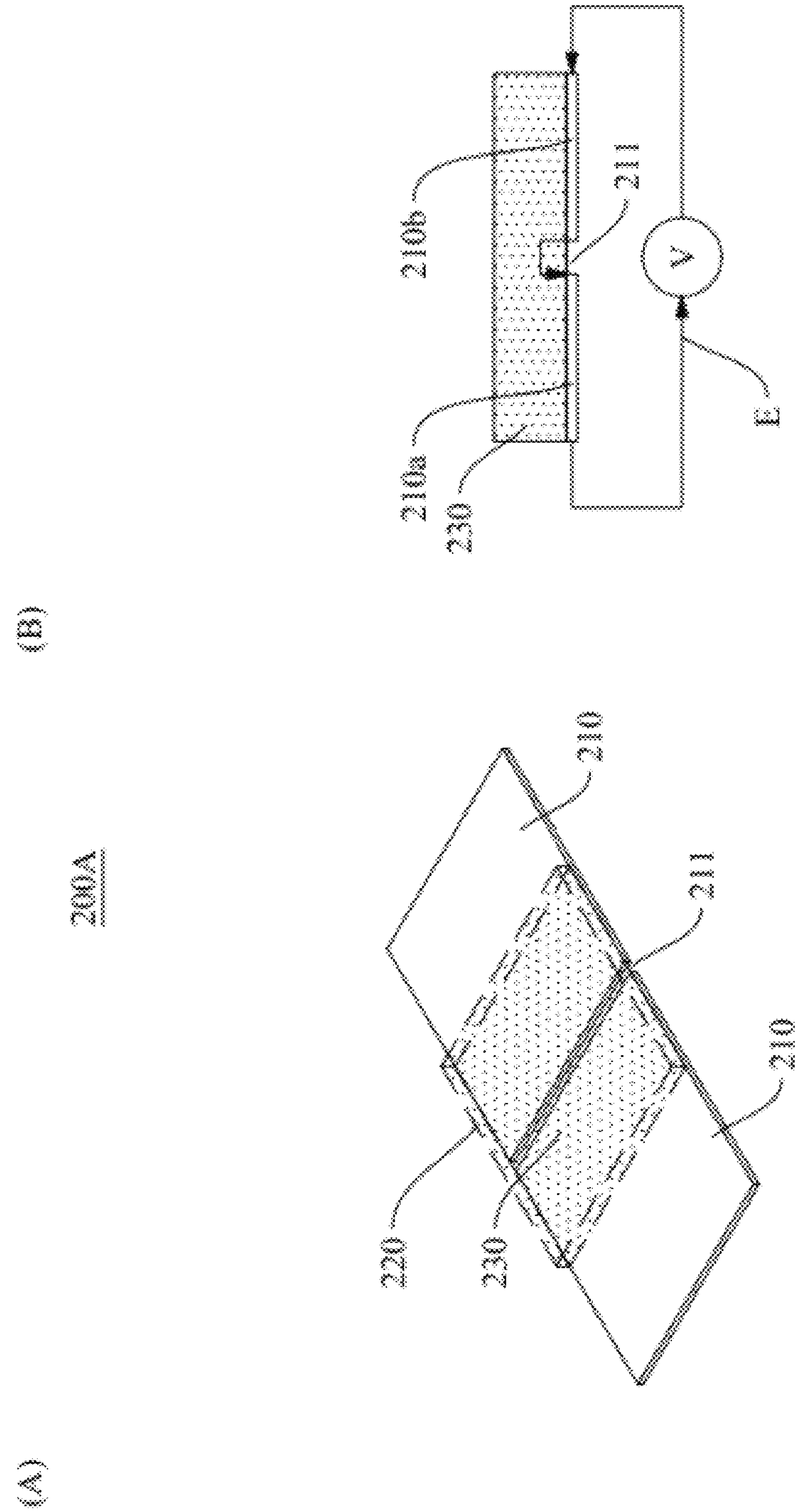
【FIG. 2】

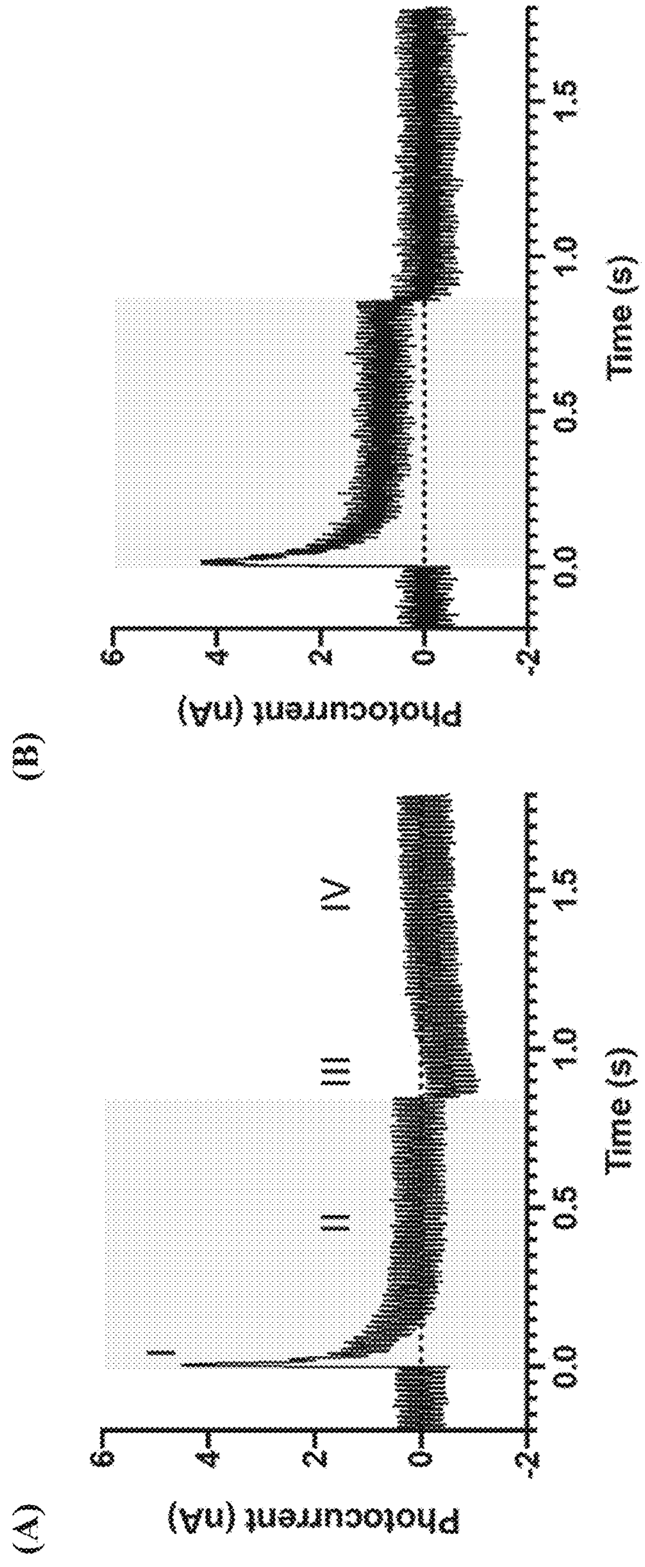
【FIG. 3】

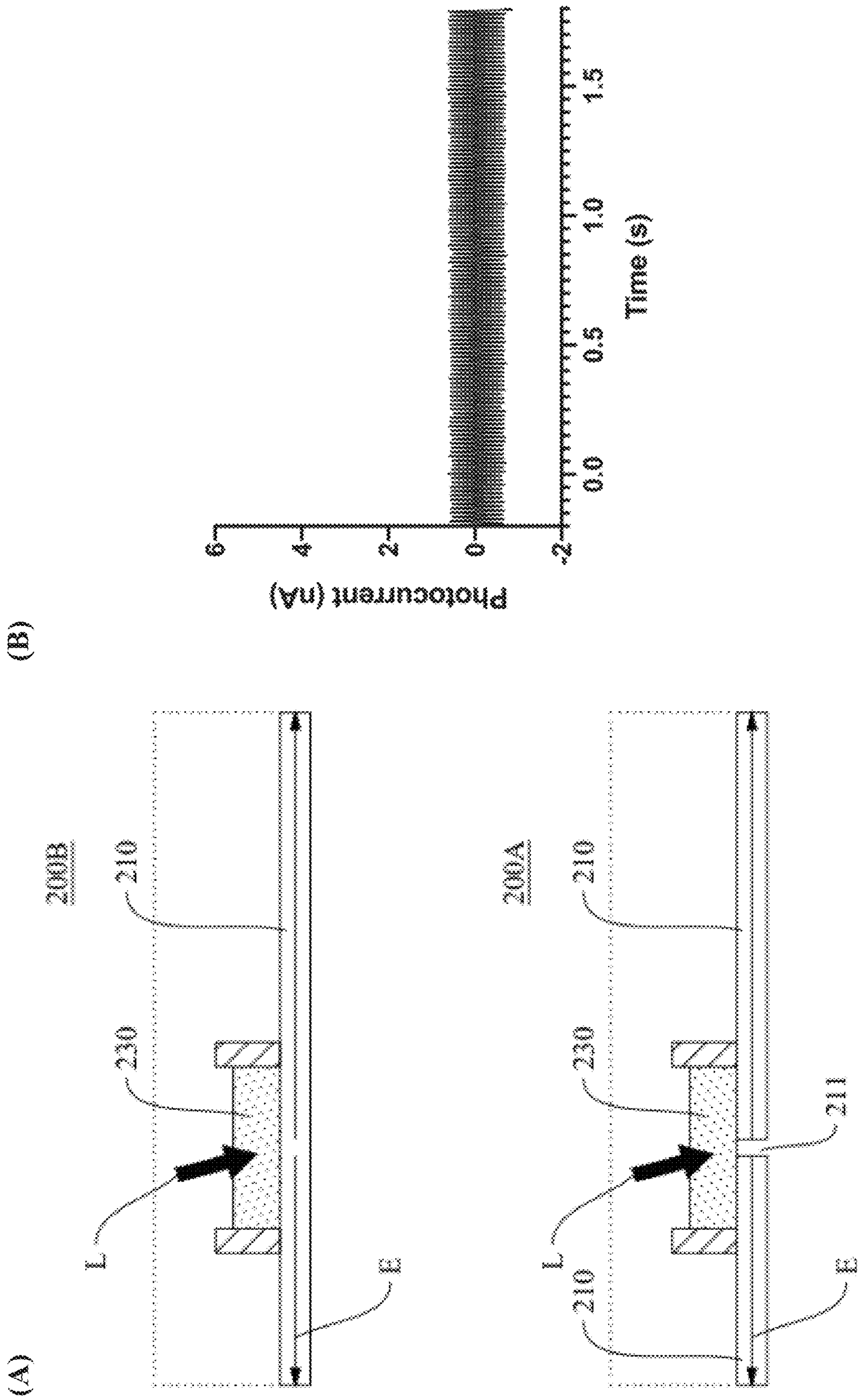
【FIG. 4A】

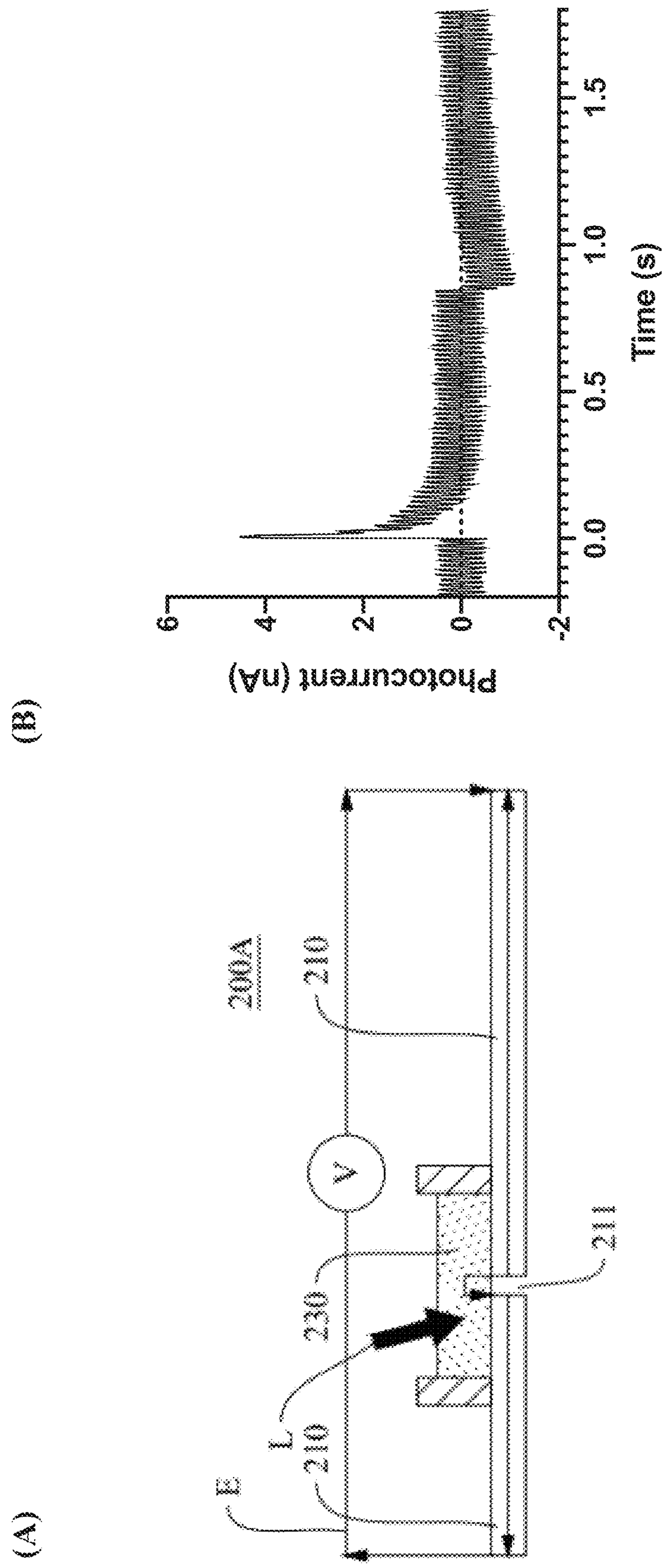
【FIG. 4B】

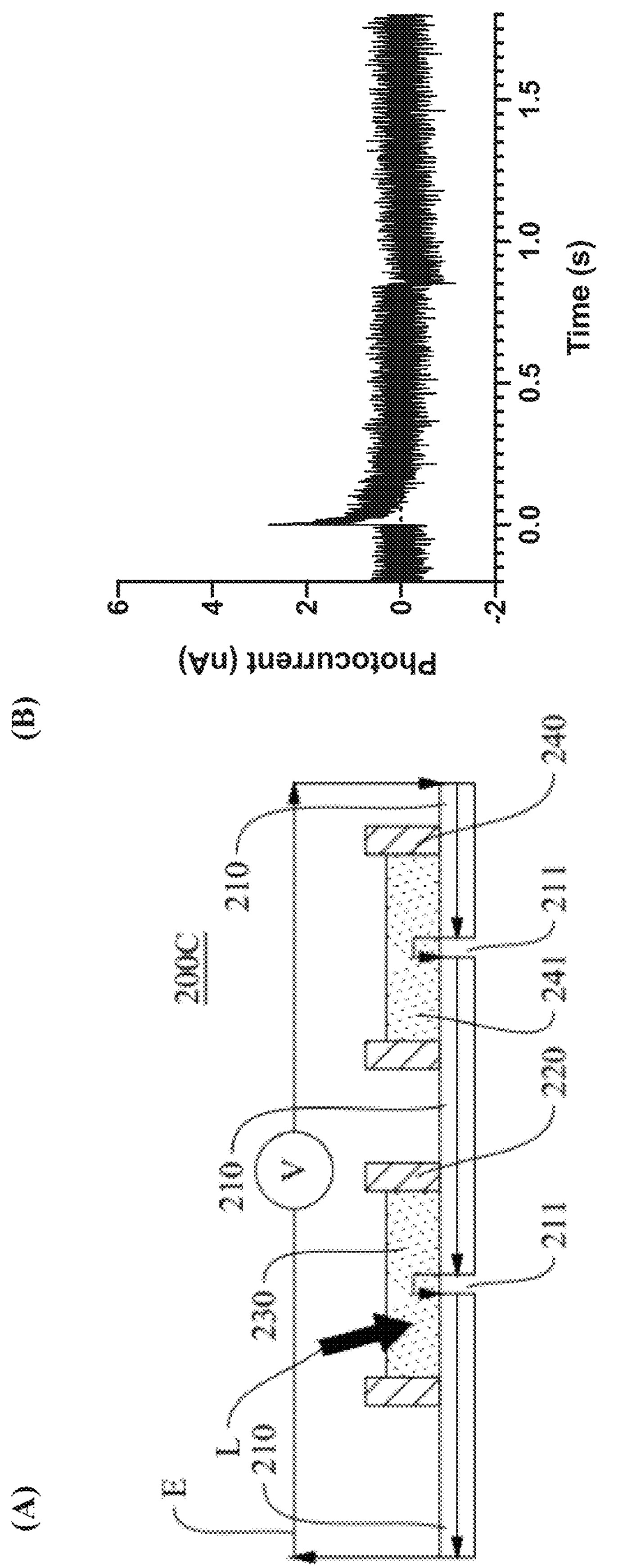
【FIG. 5】

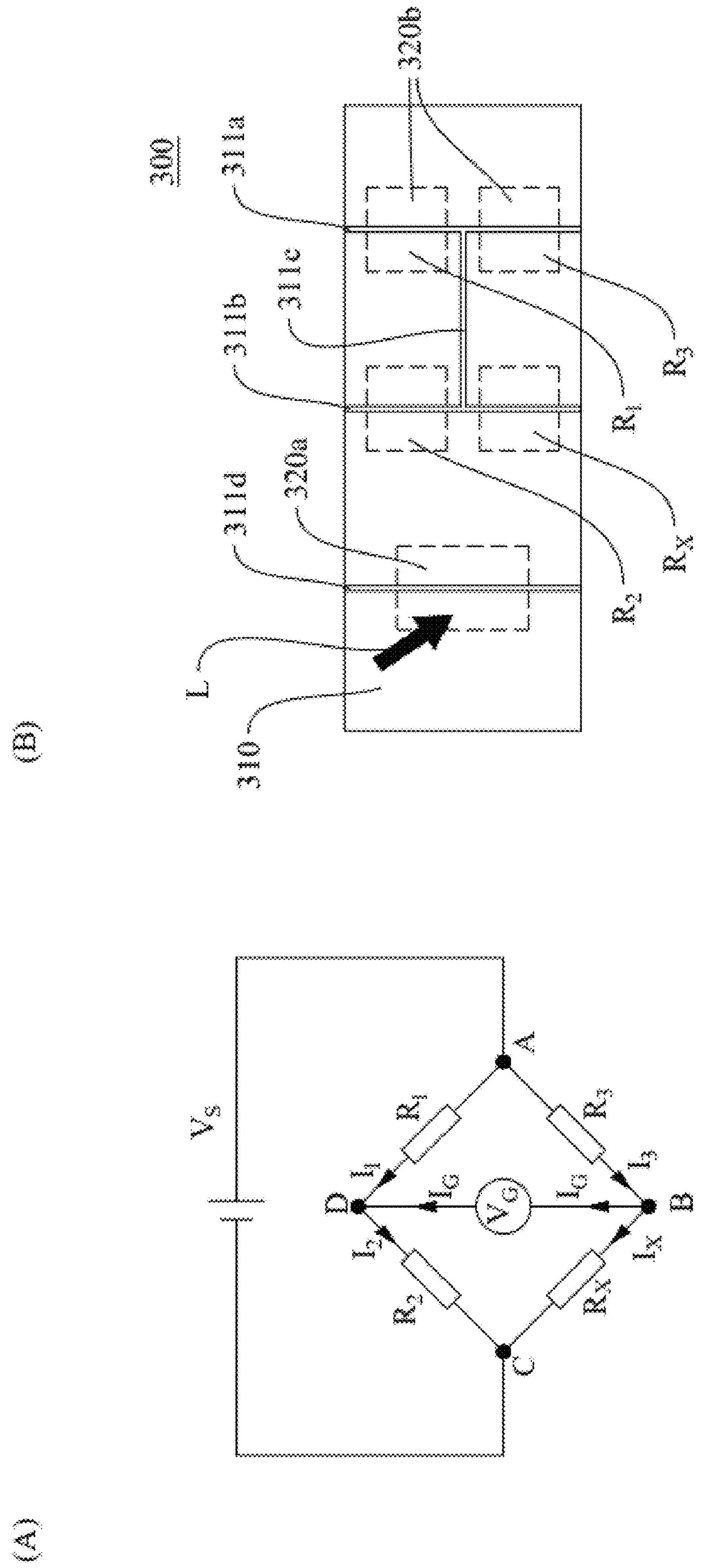
【FIG. 6】

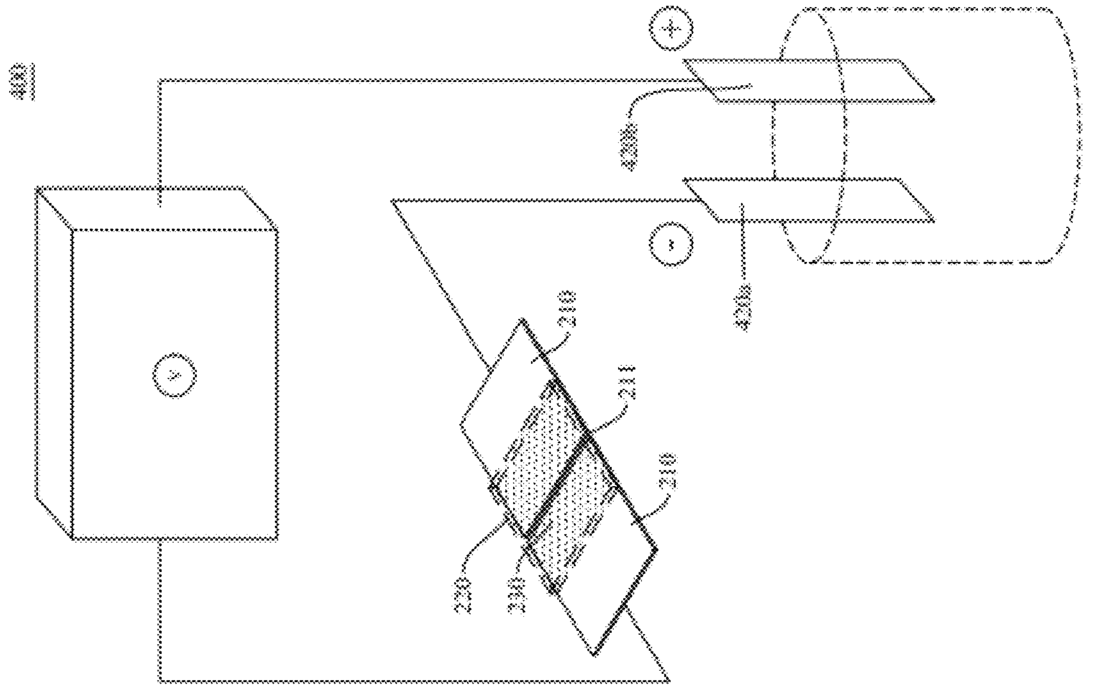
【FIG. 7】

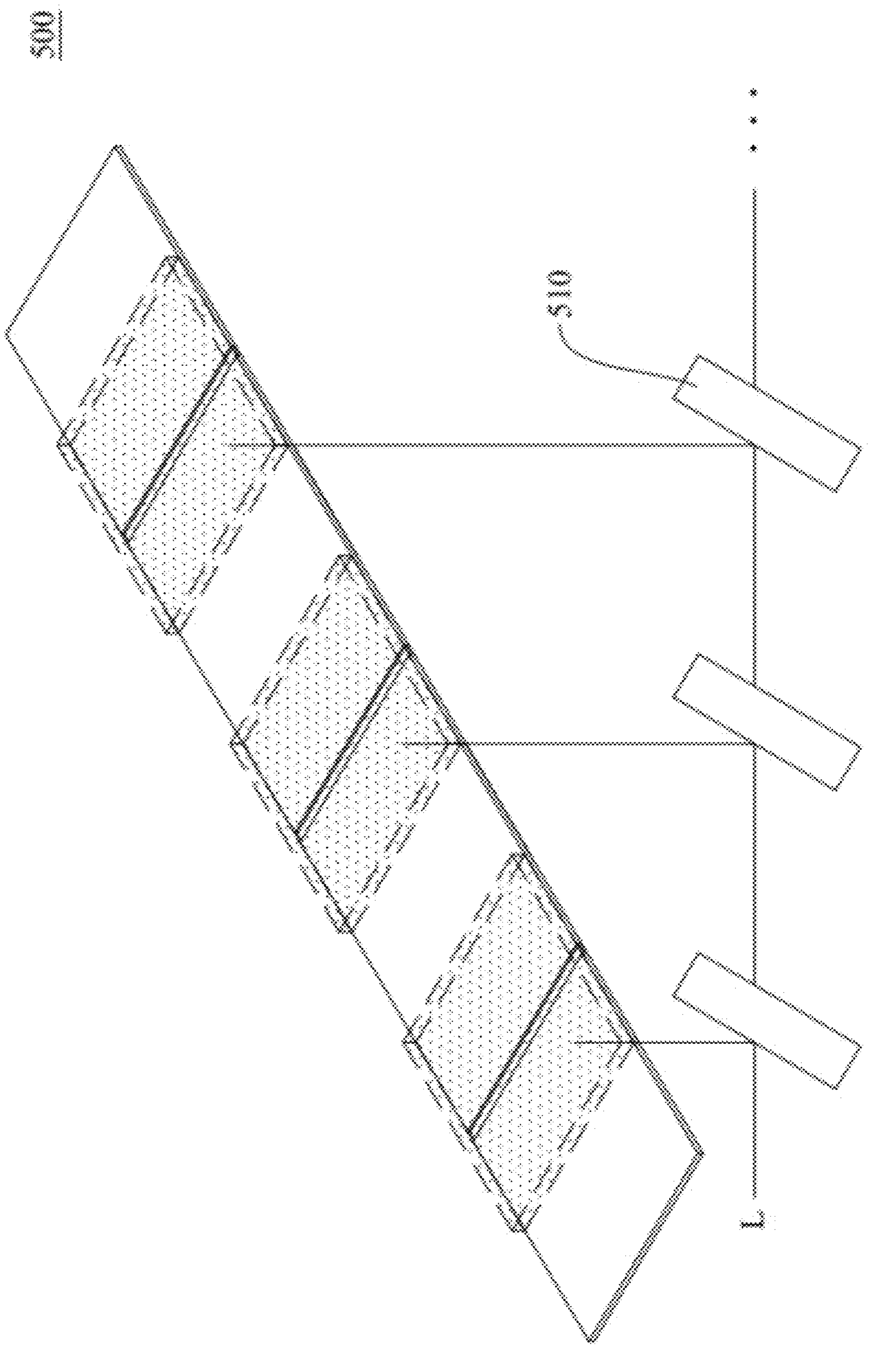
【FIG. 8A】

600
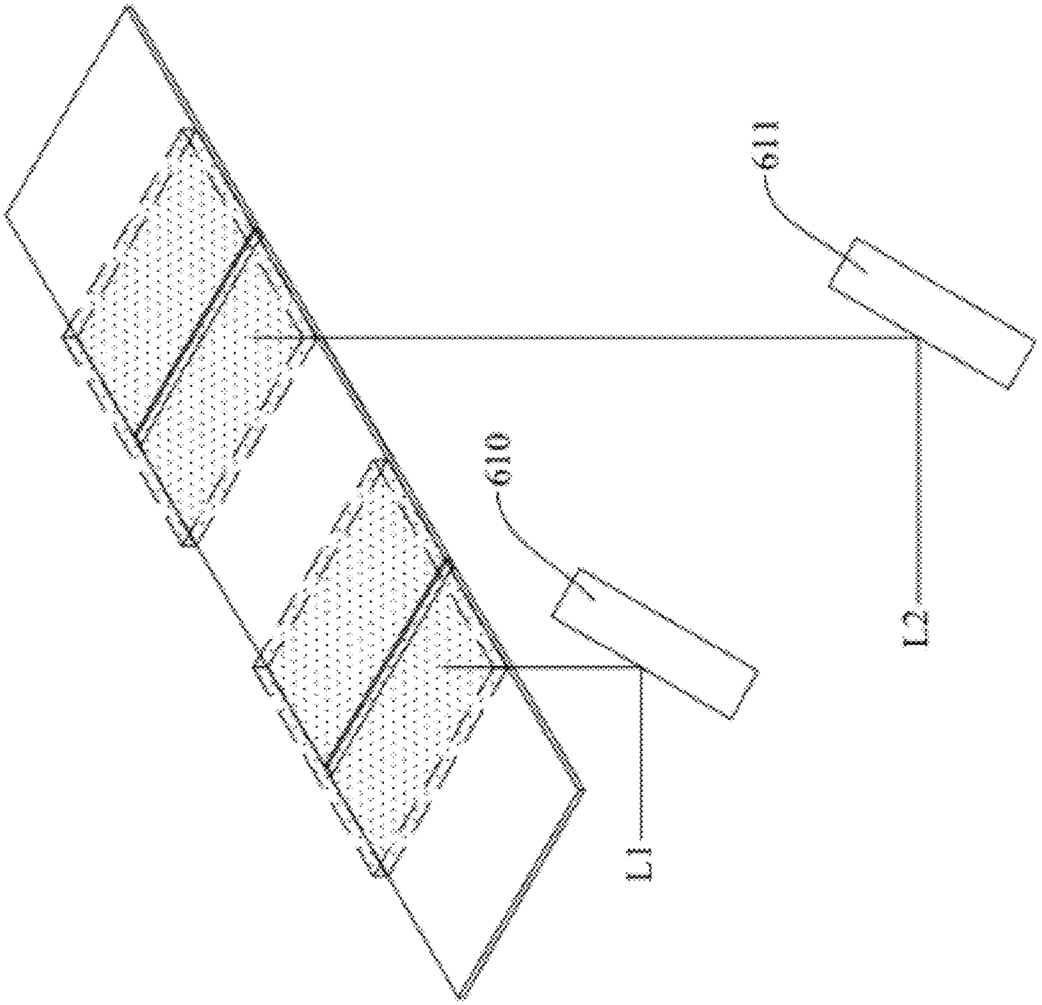
【FIG. 8B】

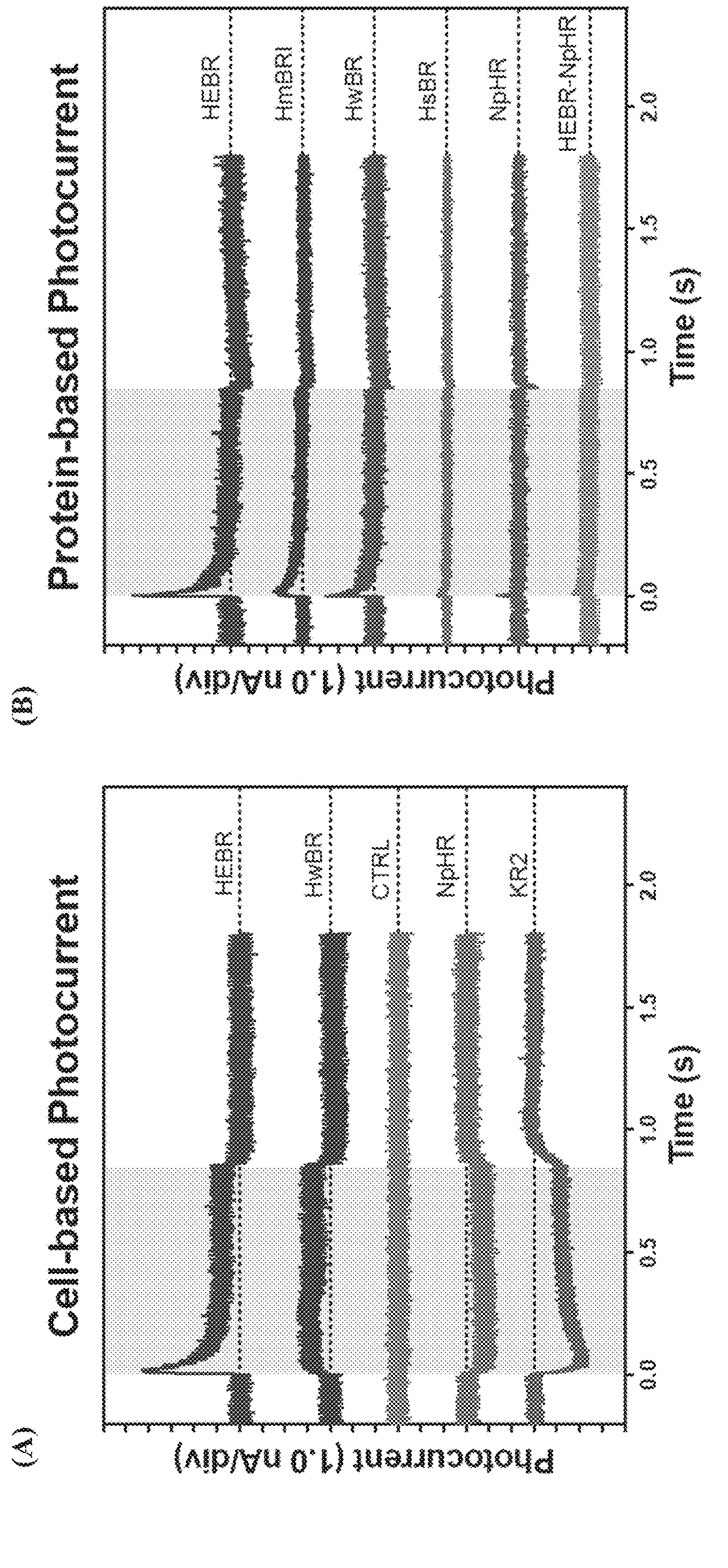
【FIG. 9】
(A)
Cell-based Photocurrent
Photocurrent (1.0 nA/div)
Time (s)
HEBR
HwBR
CTRL
NpHR
KR2
(B)
Protein-based Photocurrent
Photocurrent (1.0 nA/div)
Time (s)
HEBR
HmBRI
HwBR
HsBR
NpHR
HEBR-NpHR
【FIG. 9】

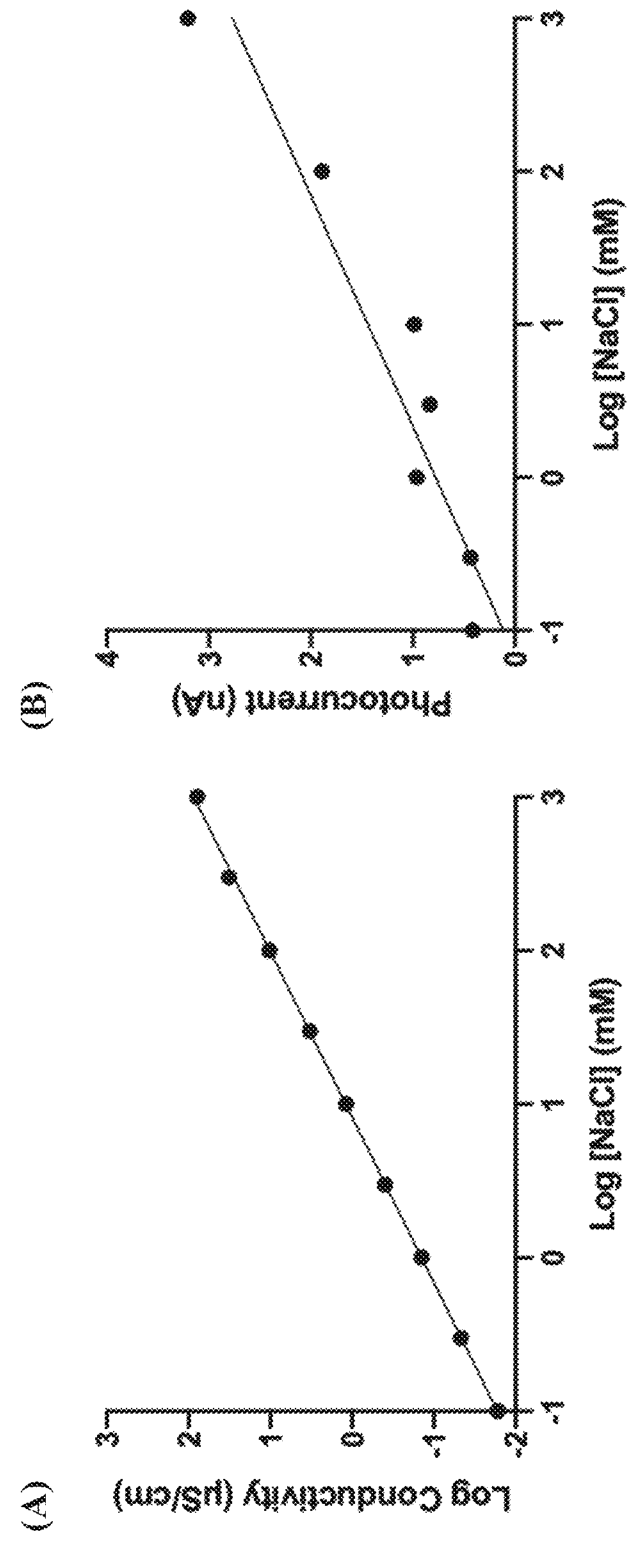
【FIG. 10】

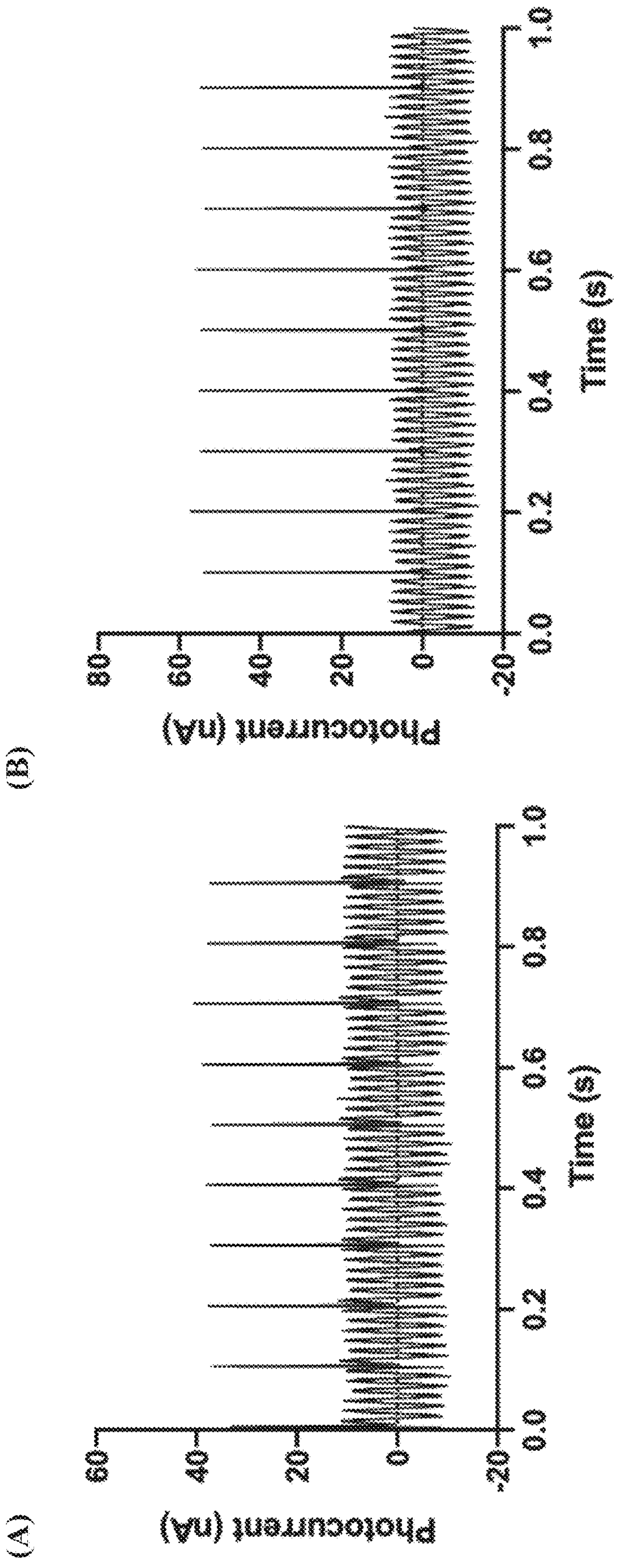
【FIG. 11】

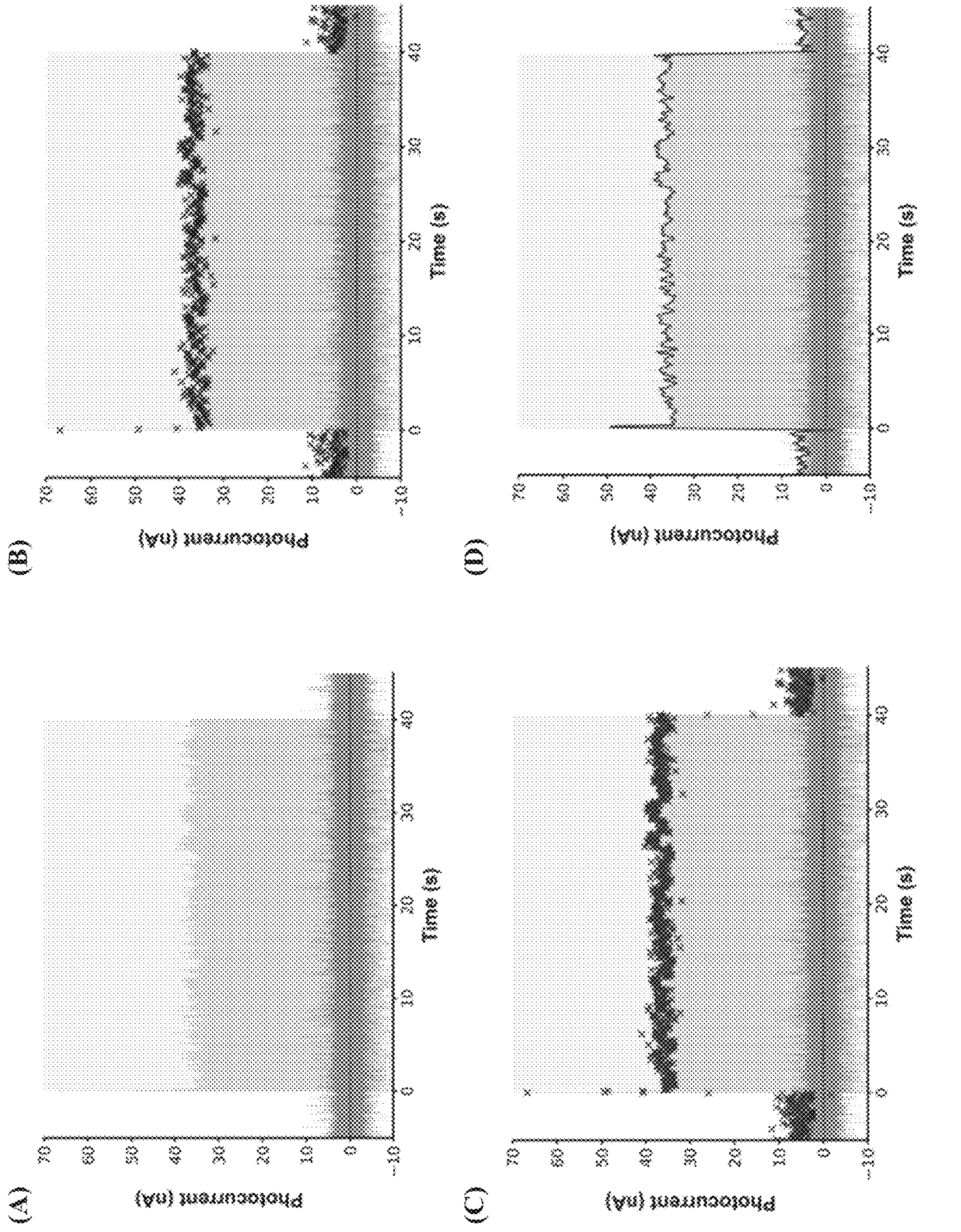
【FIG. 12】

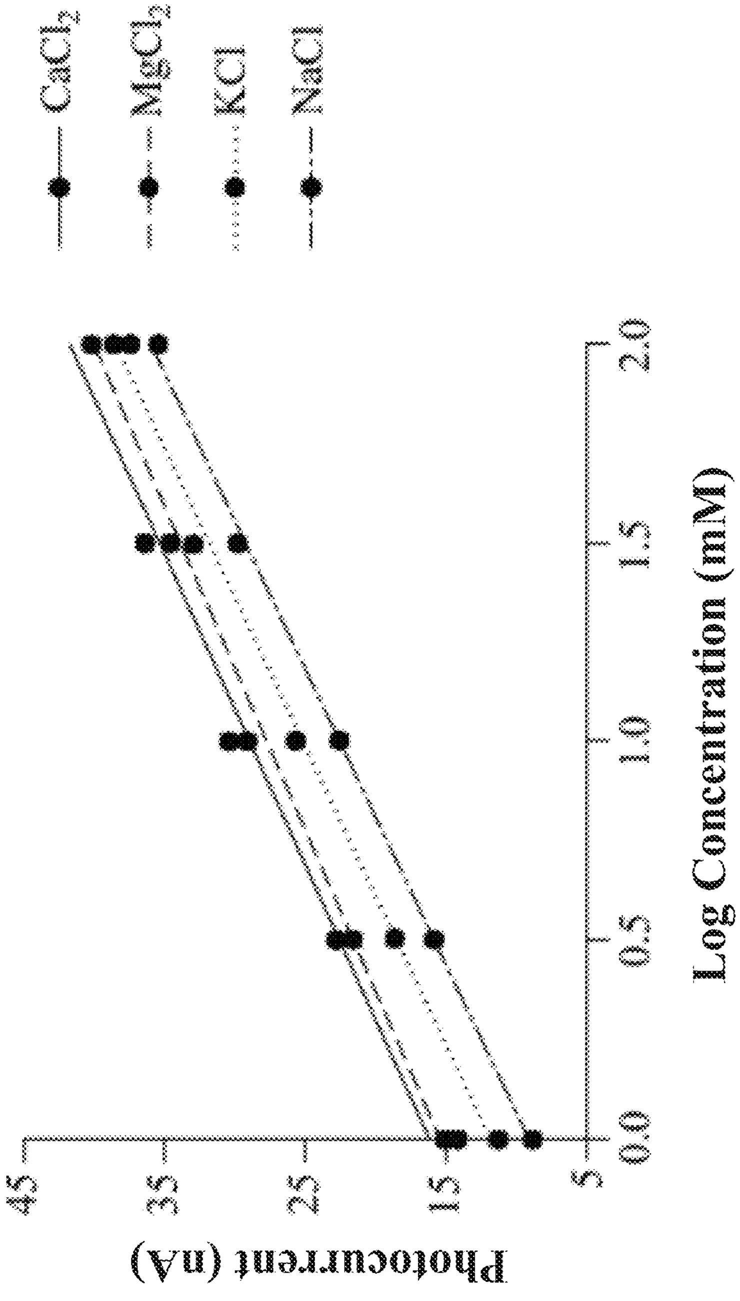
【FIG. 13】

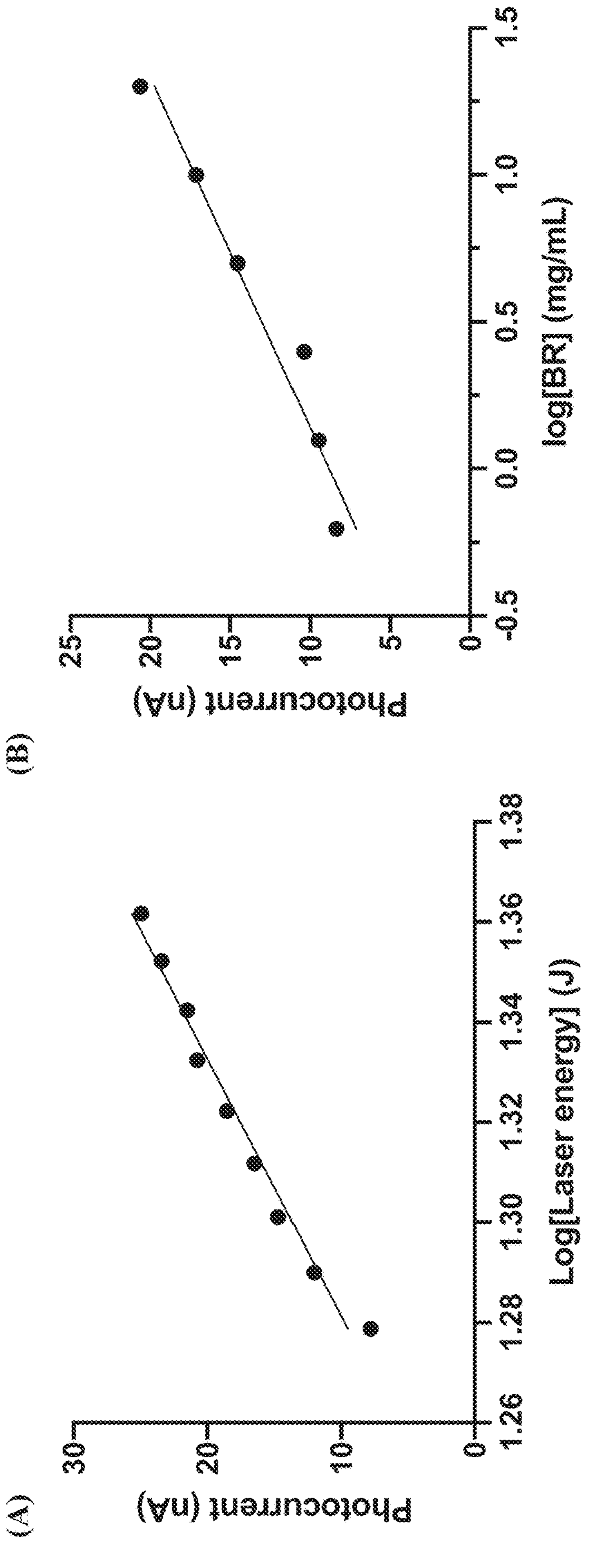
【FIG. 14】

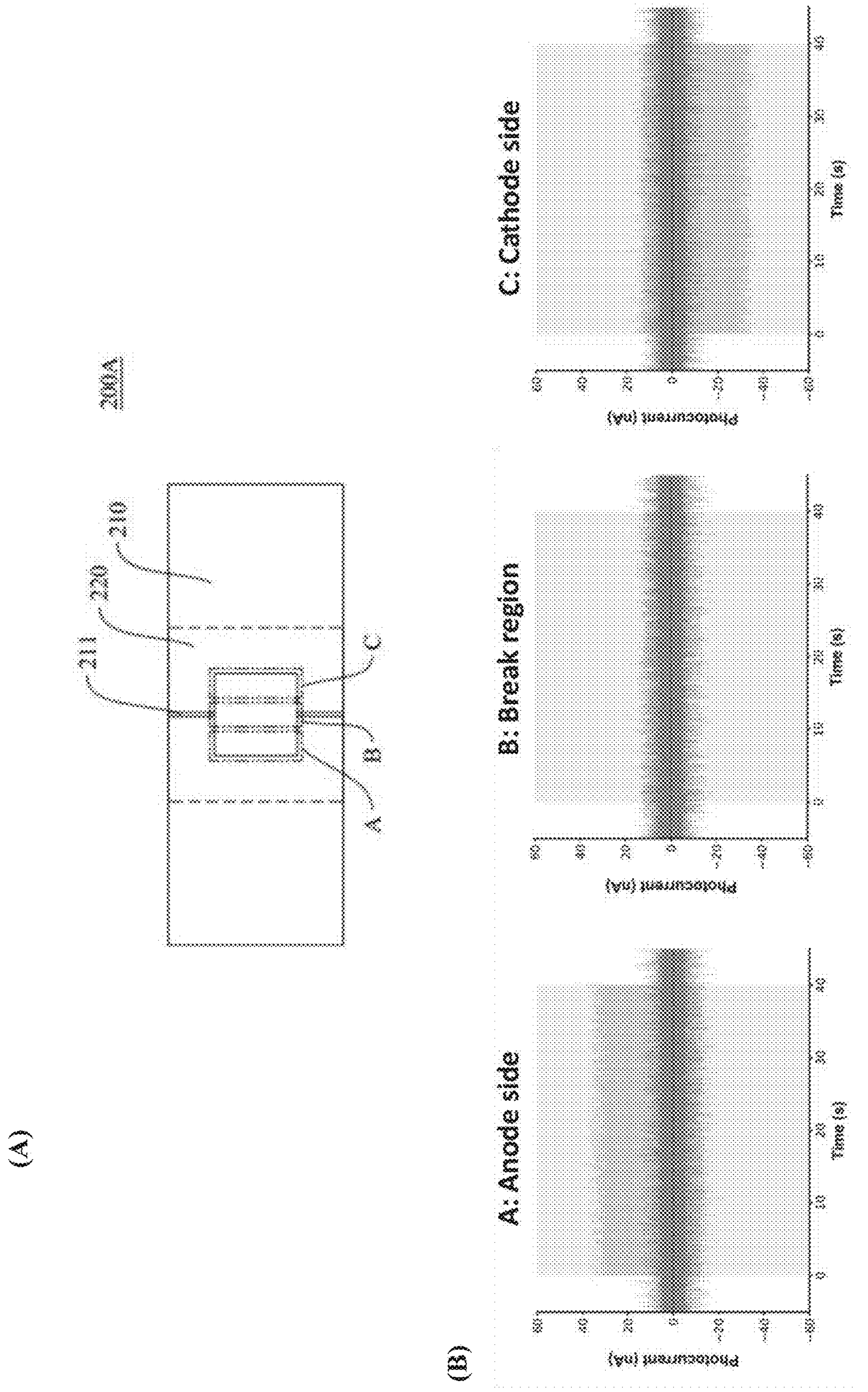
【FIG. 15】

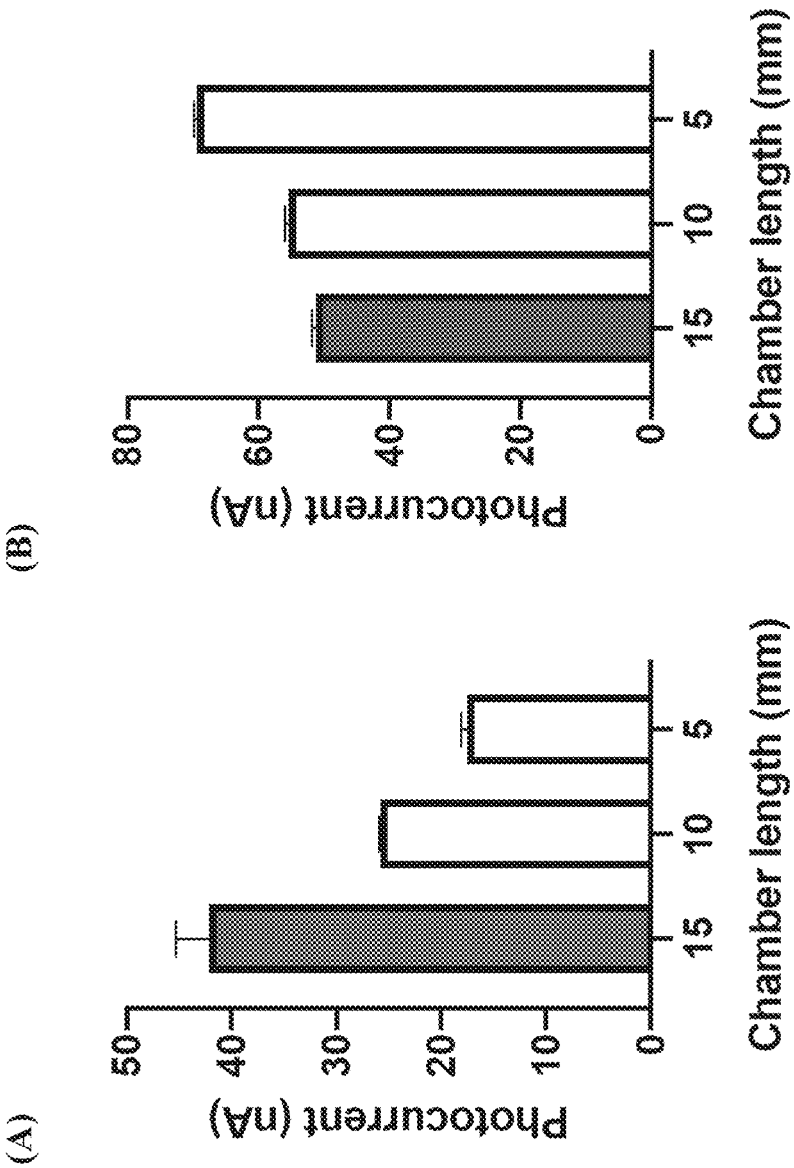
【FIG. 16】

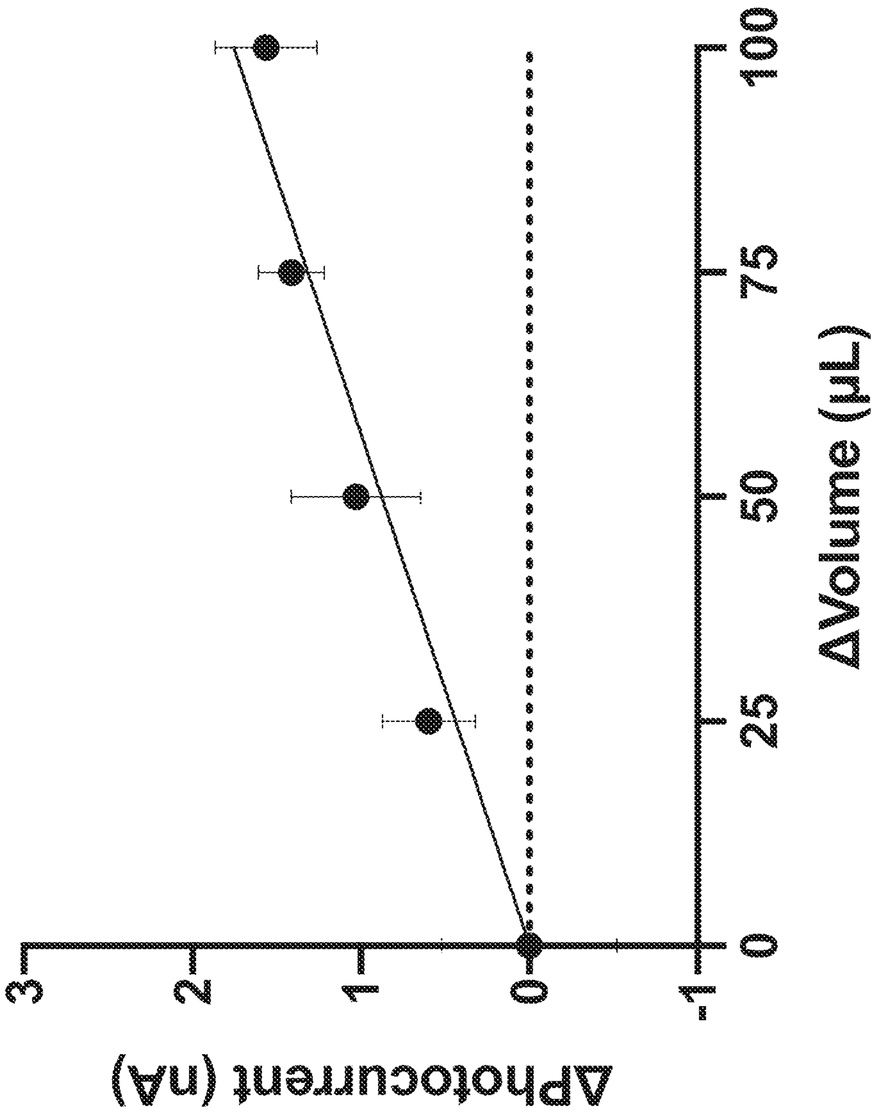
【FIG. 17】

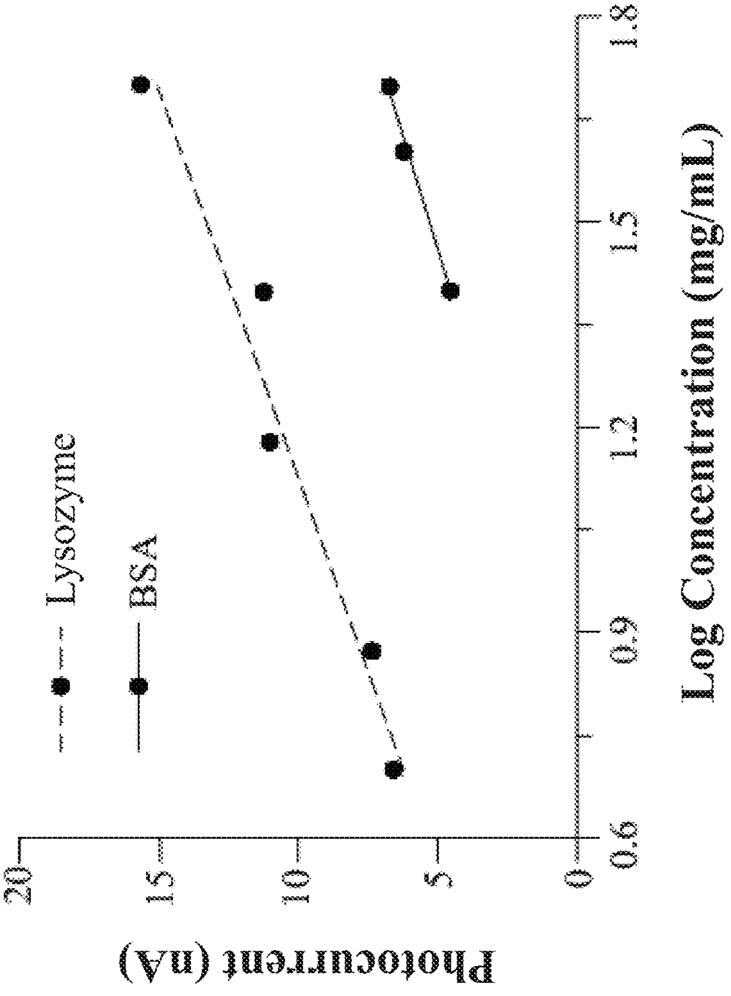
【FIG. 18】

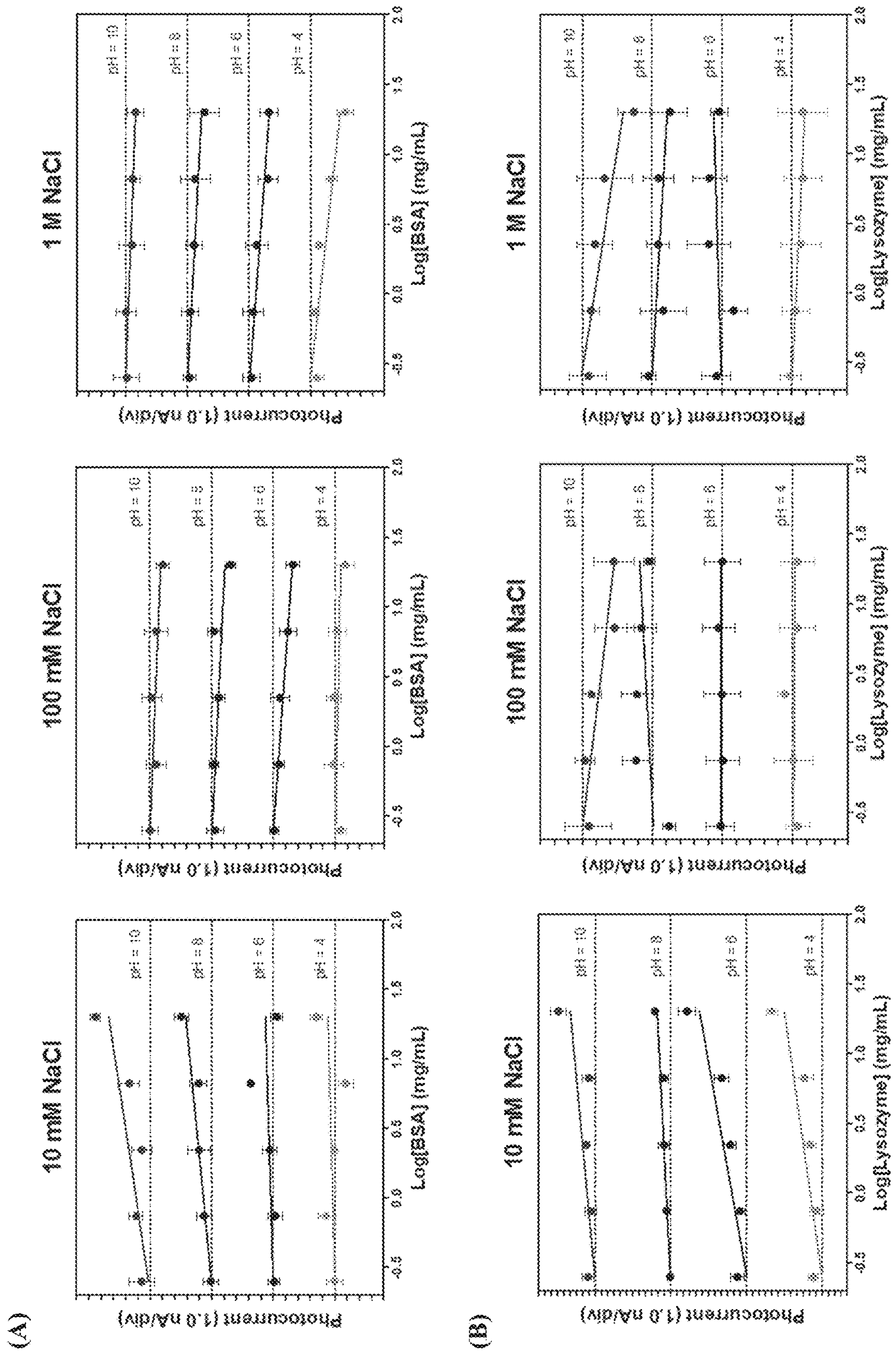
(A)
10 mM NaCl
100 mM NaCl
1 M NaCl
Photocurrent (1.0 nA/div)
Log[BSA] (mg/mL)
pH = 10
pH = 8
pH = 6
pH = 4
(B)
10 mM NaCl
100 mM NaCl
1 M NaCl
Photocurrent (1.0 nA/div)
Log[Lysozyme] (mg/mL)
pH = 10
pH = 8
pH = 6
pH = 4
【FIG. 19】

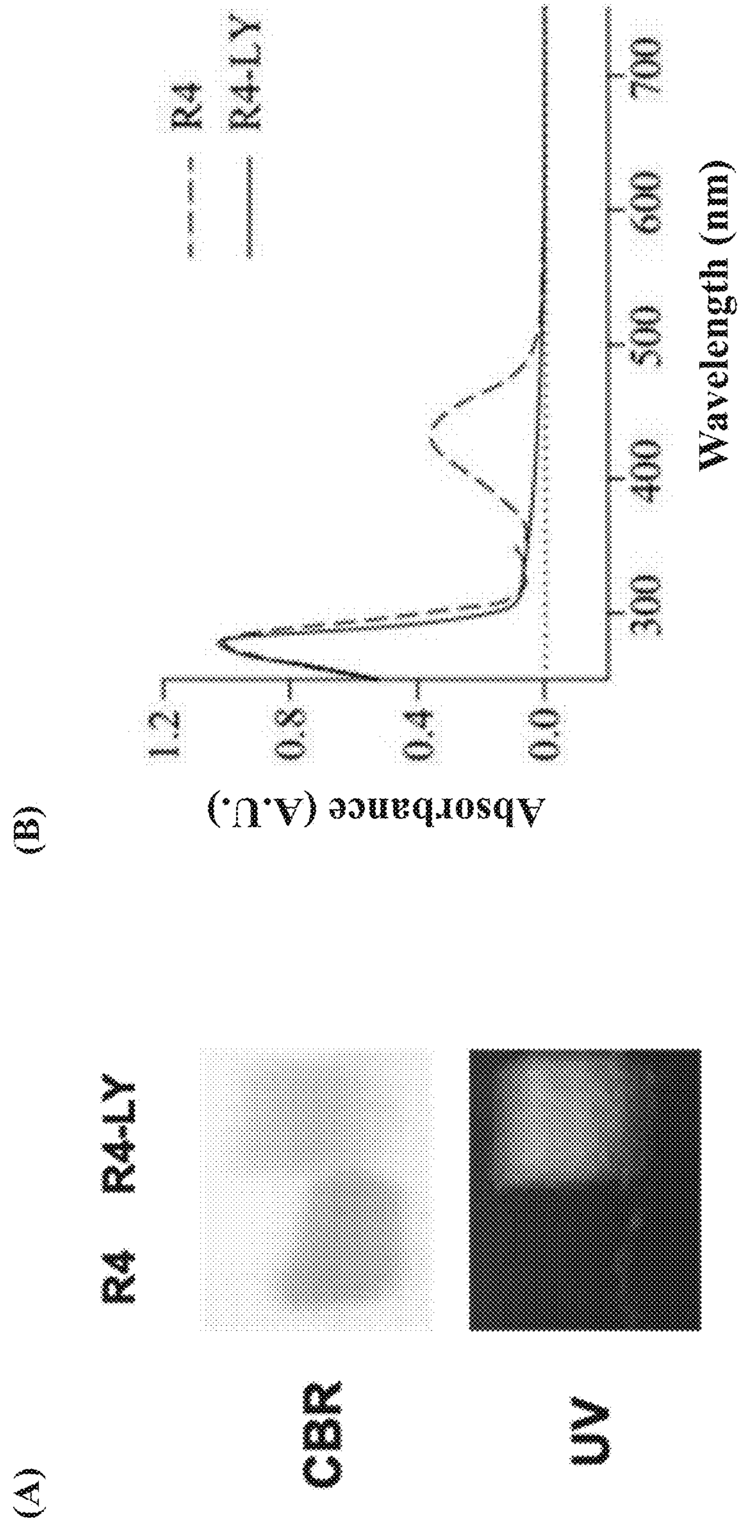
【FIG. 20】

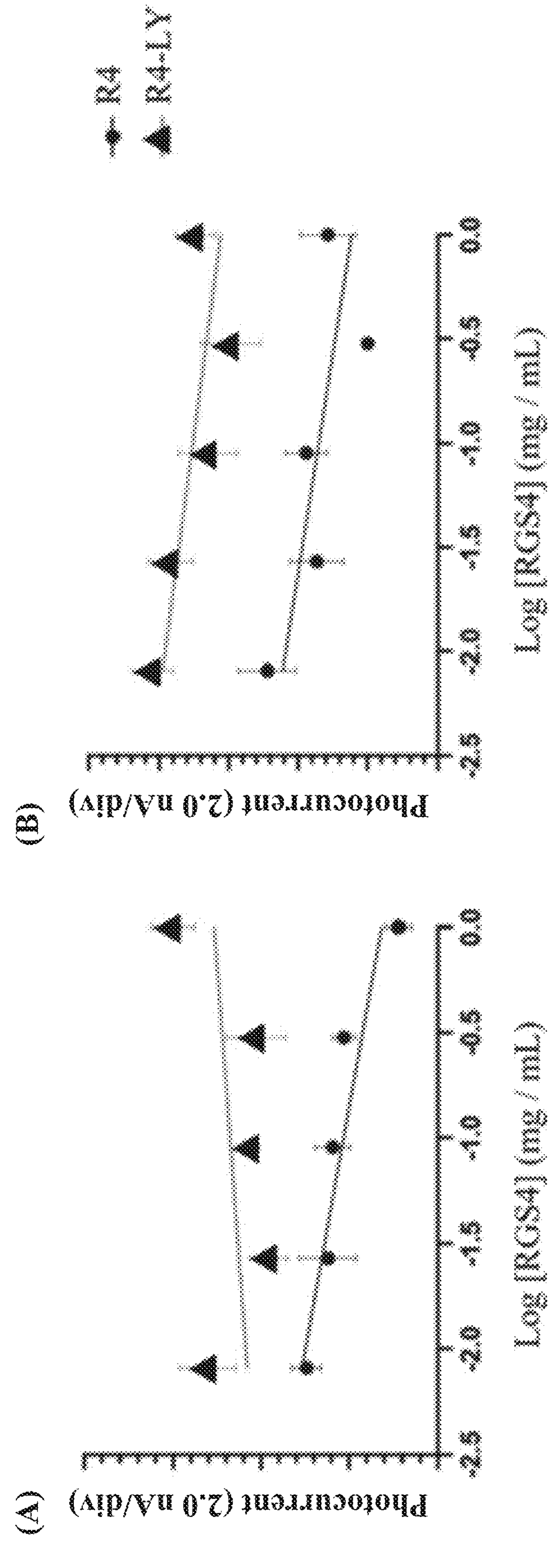
【FIG. 21】

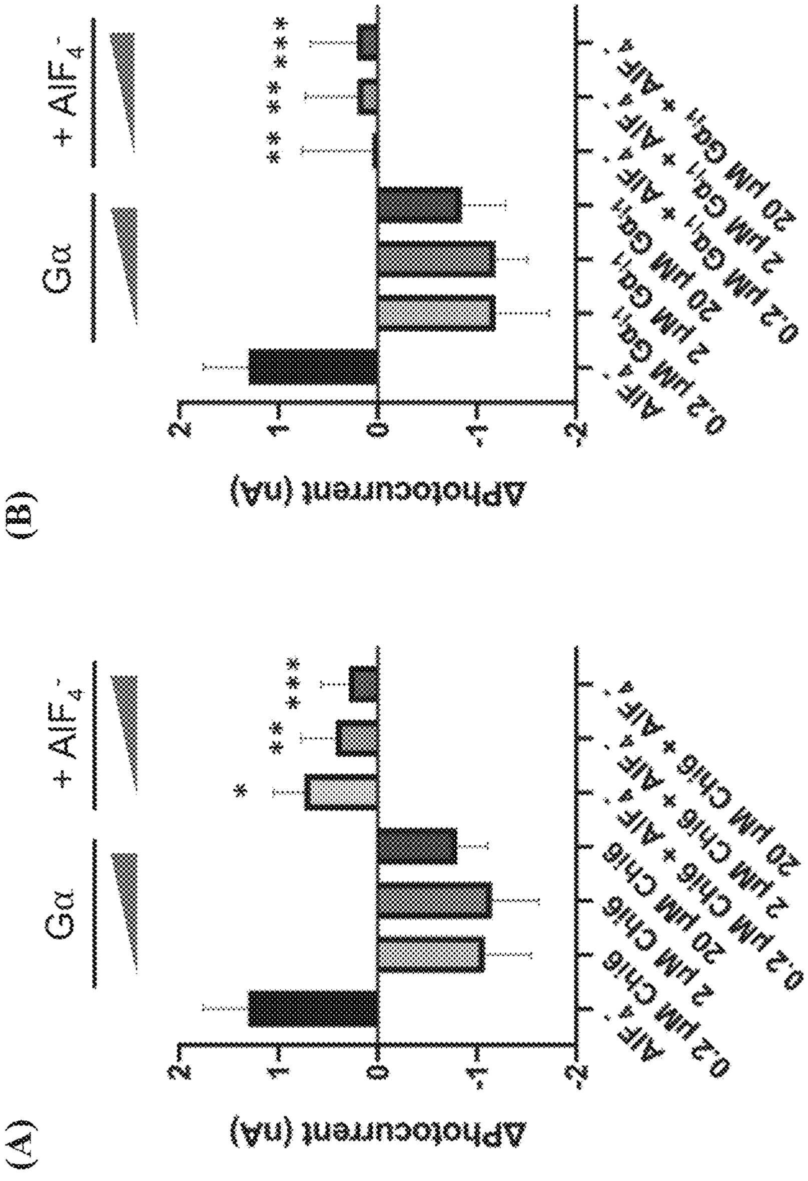
【FIG. 22】

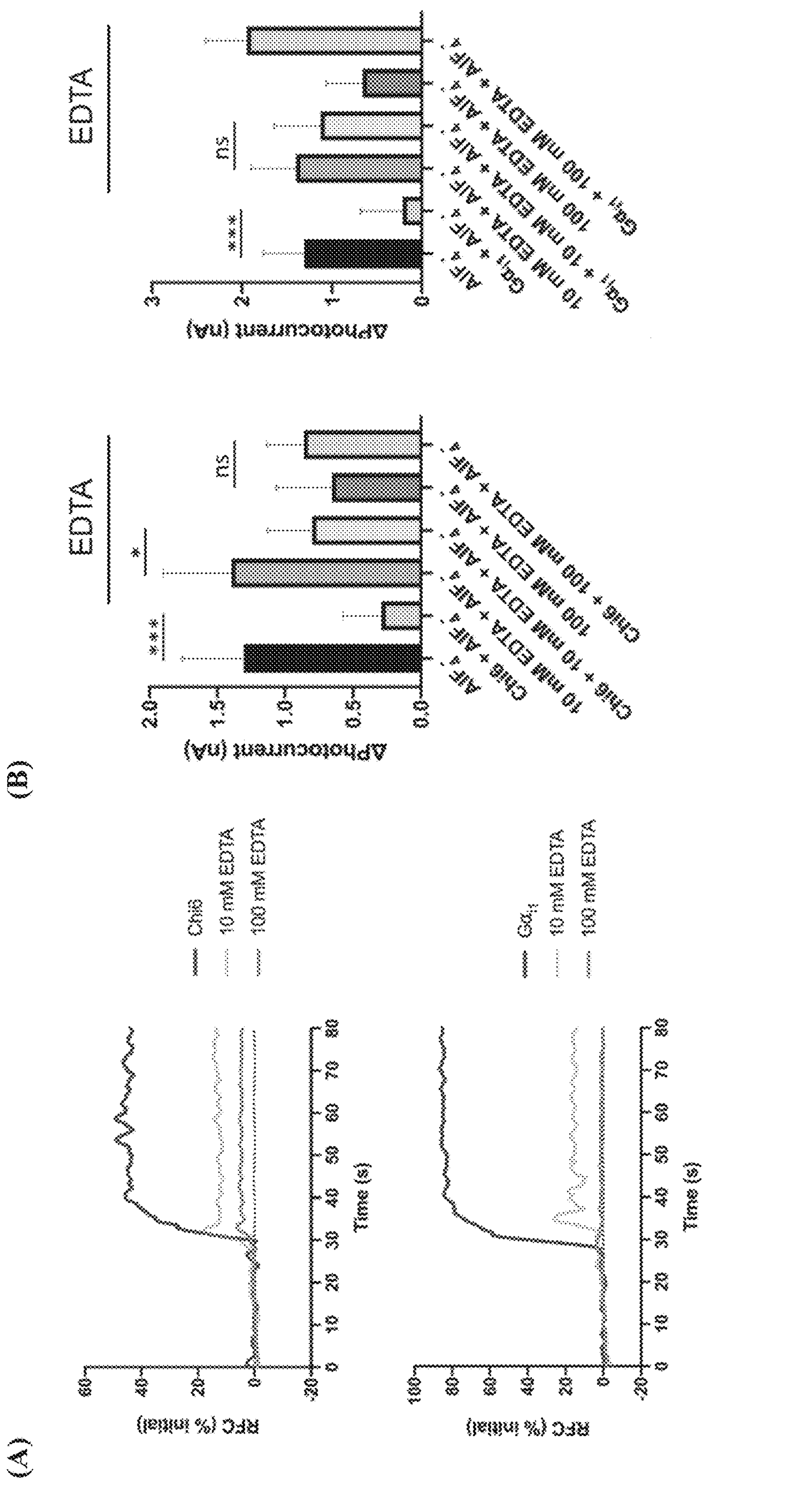
【FIG. 23】

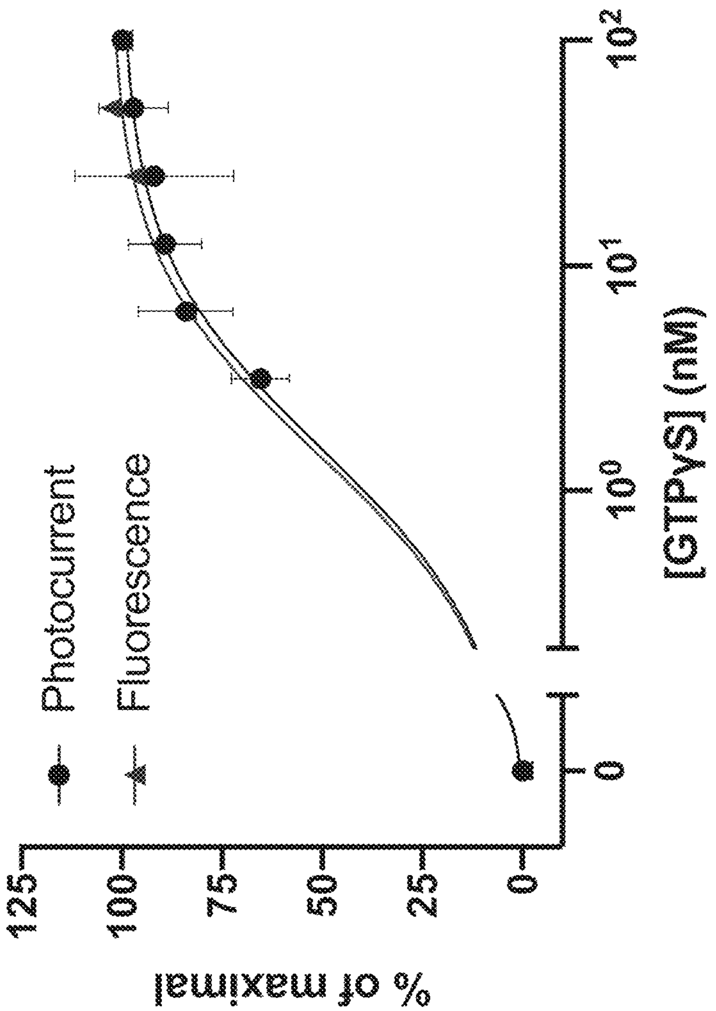
【FIG. 24】

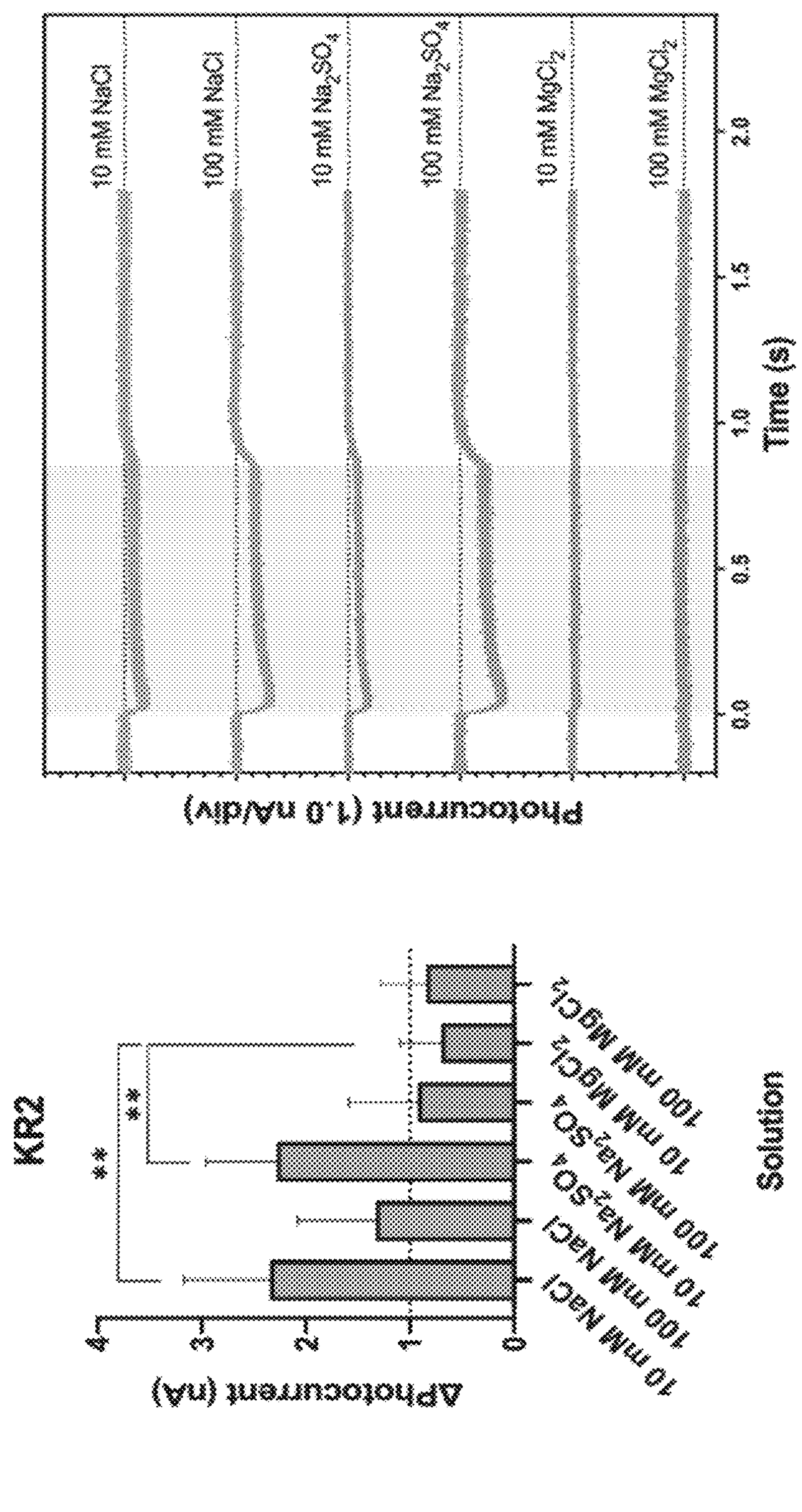
【FIG. 25A】

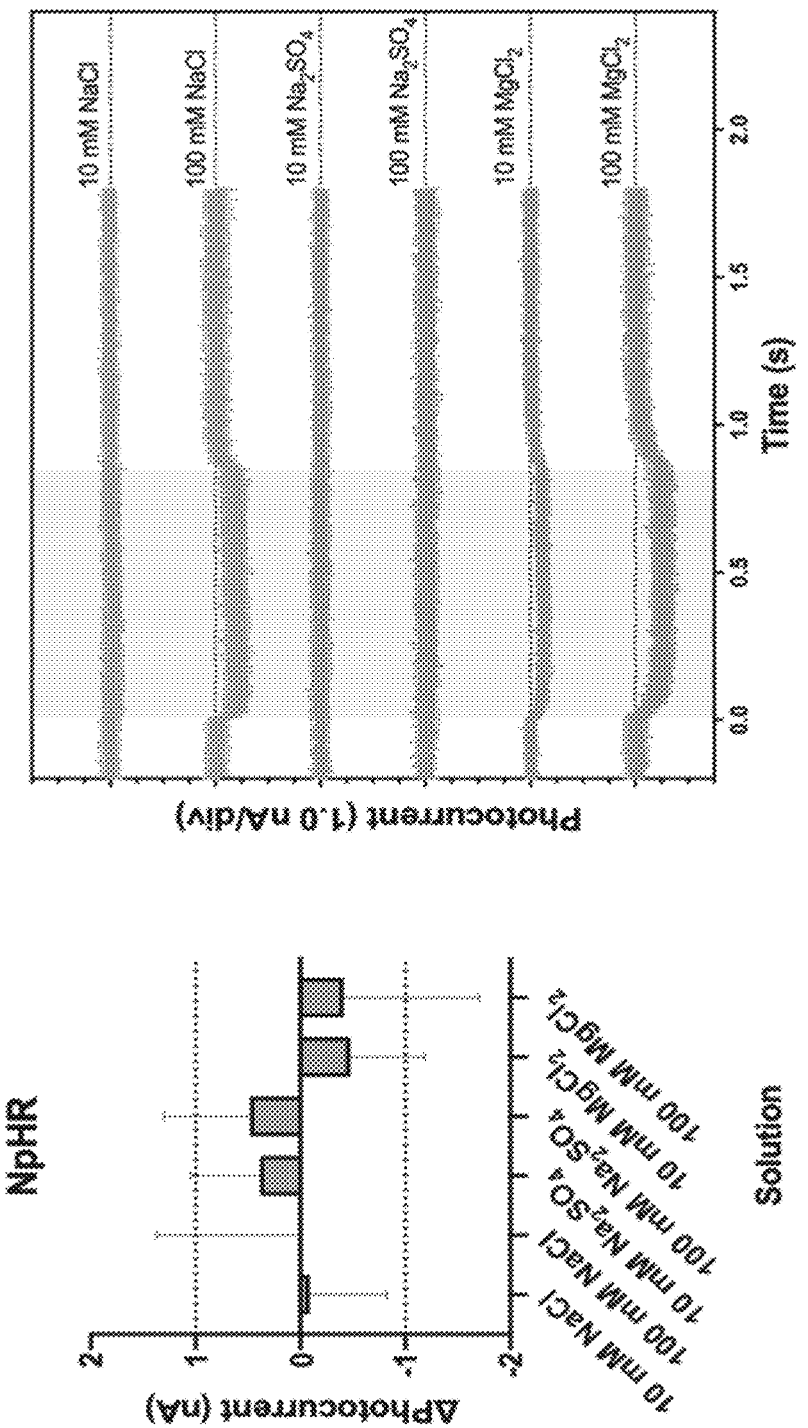
【FIG. 25B】

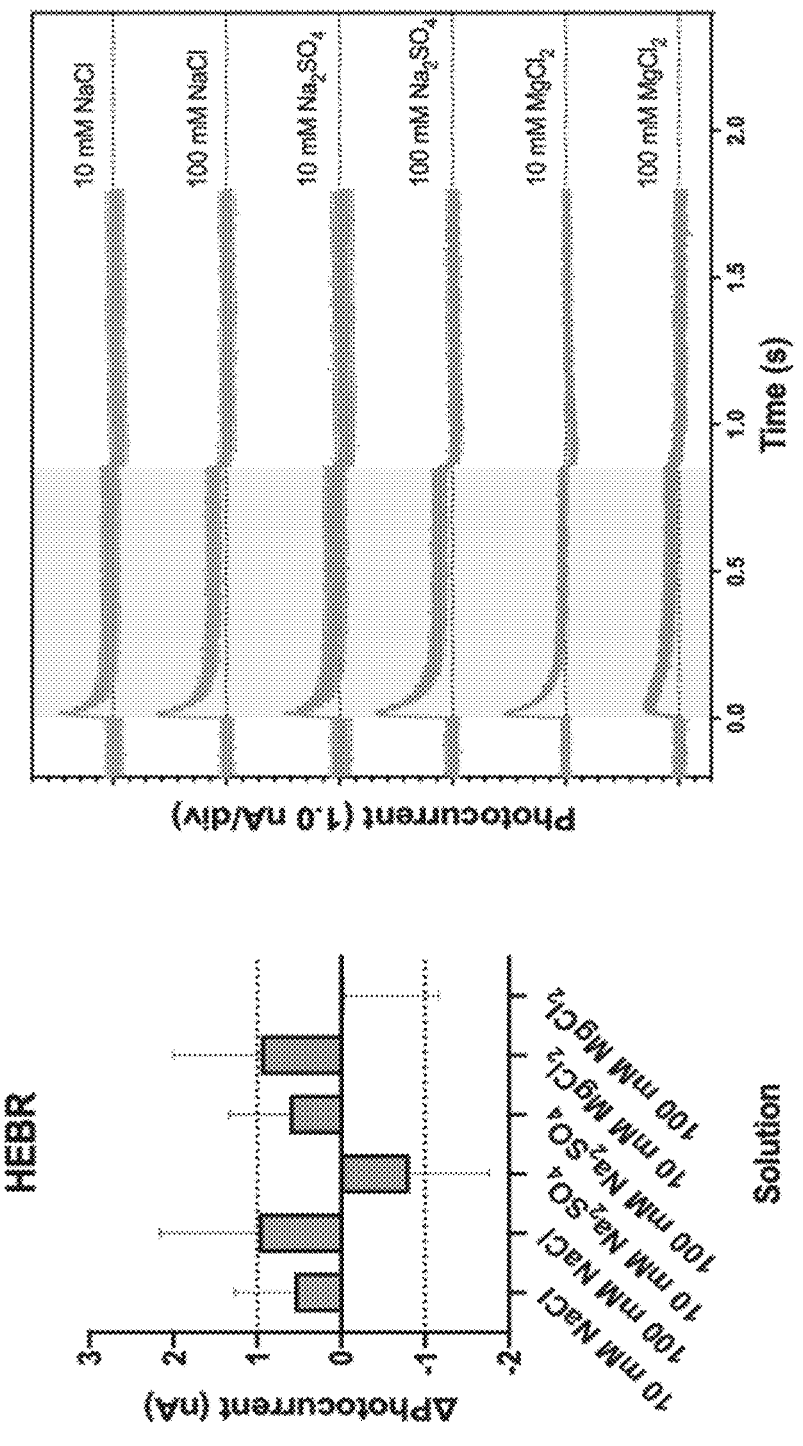
【FIG. 25C】

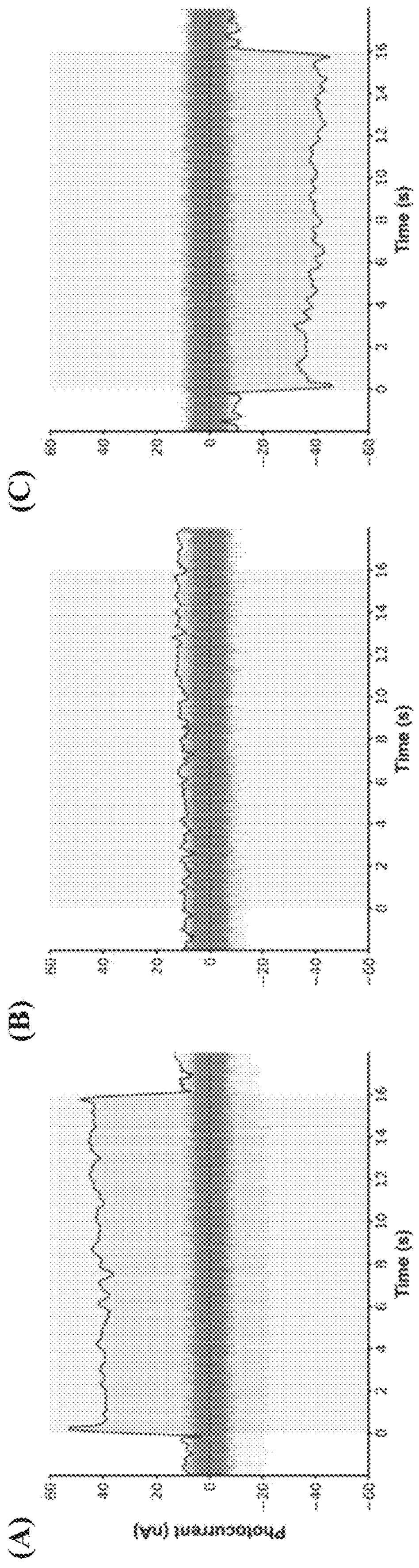
【FIG. 26】

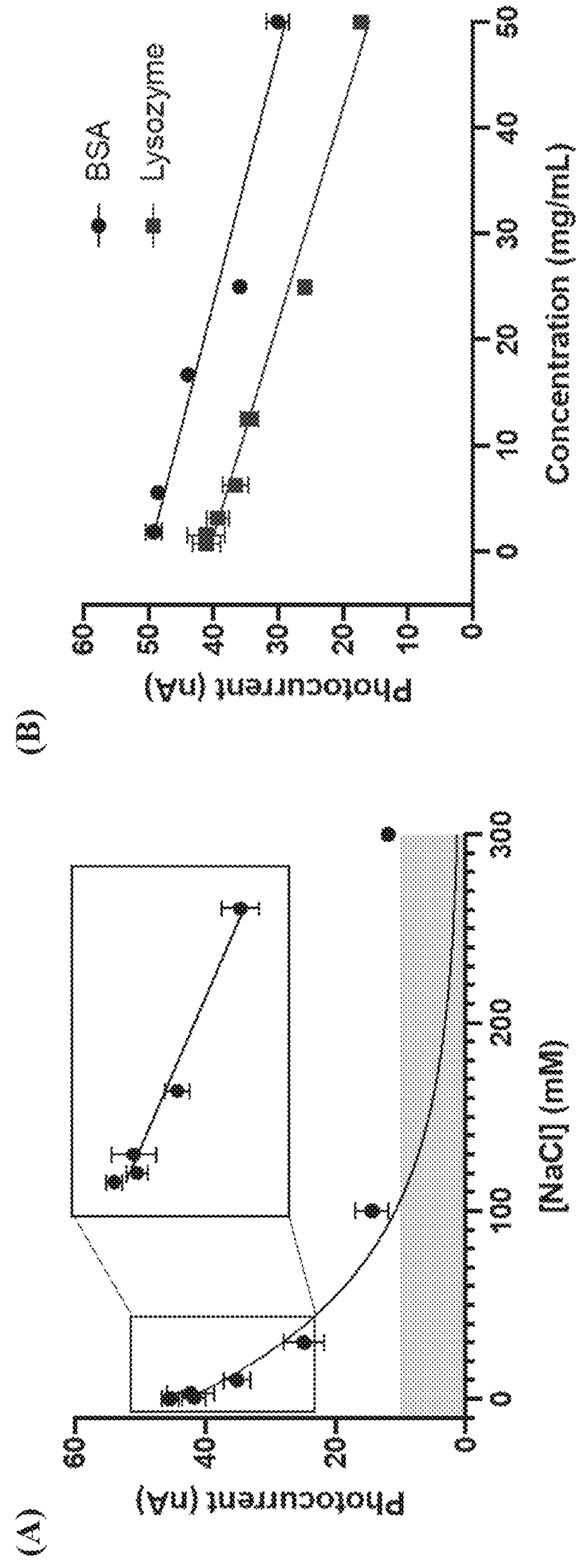
【FIG. 27】

CURRENT AND RESISTANCE SENSOR

BACKGROUND OF THE INVENTION

1. Technical Field

The present invention relates to a current and resistance sensor, in particular to a biological current and resistance sensor; however, the invention is not limited thereto.

2. Description of Related Art

The phenomenon of life is composed of countless biochemical reactions, and through the biomolecular interactions, numerous functions and features in living organisms are created. Therefore, understanding of the interactions between biomolecules helps gain insight into the mechanisms of biological functions.

Some significant technologies have provided reliable screening of biomolecular interactions, including analytical ultracentrifuge (AUC), circular dichroism spectroscopy (CD), nuclear magnetic resonance spectroscopy (NMR), surface plasmon resonance (SPR), and fluorescence, etc.

However, these techniques also have shortcomings, such as non-real-time detection of molecular interaction, making the loss of details during interactions or requiring labeling or immobilization. These additional processes may change the state of the biomolecule and hinder interactions between molecules, leading to inaccurate results.

To address the above defects, there is an improved device 100 as shown in FIG. 1, which uses two indium tin oxide (ITO)-coated glass slides 110 to sandwich two chambers 120 in the middle, and the two chambers 120 are separated by a dialysis membrane 130 (FIG. 1(A)). One chamber was filled up with a photoreceptor sample 140 to measure photocurrent, and the other chamber was filled up with blank solutions 150. After the chamber containing the photoreceptor solution 140 is illuminated, the photoreceptor protein type changes, resulting in a change in the affinity of its proton-binding domain for protons and the release of protons, and the pH value in the solution changes. ITO is very sensitive to the change in pH value in the solution, and when the pH value of the solution changes, the surface potential of ITO on the glass slides 110 increases, which leads to a photo-induced current E (FIG. 1(B)).

BRIEF SUMMARY OF THE INVENTION

While the market has been supplied with the conventional device described above, the device has a relatively complicated design and incurs a relatively high cost because it not only requires two indium tin oxide (ITO)-coated glass slides that serve as an electrically conductive material to allow an electric current to flow through the device, but also needs a dialysis membrane sandwiched between the two glass slides. Furthermore, the current generation chamber must not contain a pH buffer, or the ITO cannot detect changes in the pH value of the solution. As the two chambers are separated by the dialysis membrane, the other chamber must also be free of any pH buffer, and this limits the possibilities of measurement. Moreover, the conventional device can test only one sample at a time and does not allow the addition of more substances during the measuring process, so the number of test samples is restricted.

In view of the above, the present invention provides a system for monitoring the interactions between natural-state biomolecules in real time with low sample consumption.

Taking advantage of the phenomenon that the surface charges of biomolecules will increase or decrease during biomolecule interactions and thereby cause a change in electrical resistance, the monitoring system can compensate for the deficiencies of the prior art.

An aspect of the present invention provides a current and resistance sensor, comprising: a photo-induced-voltage-generating solution chamber for receiving a photoreceptor-protein-containing solution; and a compound layer on one side of the photo-induced-voltage-generating solution chamber, wherein the compound layer is responsive to changes in the amount of protons in the solution, and the compound layer is provided with a gap corresponding in position to the photo-induced-voltage-generating solution rendered chamber and is thus discontinuous within the photo-induced-voltage-generating solution chamber.

In some embodiments, the photoreceptor-protein is bacteriorhodopsin.

In some embodiments, the bacteriorhodopsin is derived from *Haloarcula marismortui, Halobacterium salinarum* or *Haloquadratum walsbyi.*

In some embodiments, the compound layer is divided by the gap into two ends, and the two ends are connected to a positive electrode and a negative electrode of an oscilloscope respectively.

In some embodiments, the two ends of the compound layer are electrically coupled to an amplifier and then electrically coupled to the oscilloscope.

In some embodiments, the compound layer is a coating formed by a compound of indium tin oxide (ITO), indium zinc oxide (IZO), indium tungsten oxide (IWO), or fluorine-doped tin oxide (FTO).

In some embodiments, the current and resistance sensor further comprises at least one sample chamber provided on the compound layer, wherein the compound layer is further provided with a gap corresponding to each of the at least one sample chamber and is thus rendered discontinuous within each of the at least one sample chamber.

In some embodiments, there are four said sample chambers, namely a first sample chamber ($R_1$), a second sample chamber ($R_2$), a third sample chamber ($R_3$), and a test sample chamber ($R_x$); the gaps in the compound layer that correspond respectively to the first sample chamber ($R_1$) and the third sample chamber ($R_3$) are connected to form a first gap; the gaps in the compound layer that correspond respectively to the second sample chamber ($R_2$) and the test sample chamber ($R_x$) are connected to form a second gap; and a portion of the first gap that lies between the first sample chamber ($R_1$) and the third sample chamber ($R_3$) and a portion of the second gap that lies between the second sample chamber ($R_2$) and the test sample chamber ($R_x$) are connected by a third gap.

In some embodiments, the compound layer has two portions separated by, and hence located respectively on two opposite sides of, the third gap and connected respectively to a positive electrode and a negative electrode of an oscilloscope.

In some embodiments, the compound layer is divided by the gap into two ends, and the two ends are connected to a pair of electrically conductive probes respectively.

In some embodiments, the conductive probe is a coating formed by a compound of indium tin oxide (ITO), indium zinc oxide (IZO), indium tungsten oxide (IWO), or fluorine-doped tin oxide (FTO).

In some embodiments, the current and resistance sensor further comprises a laser source.

In some embodiments, the current and resistance sensor further comprises at least one reflective mirror provided between the laser source and the photo-induced-voltage-generating solution chamber or a sample chamber.

In some embodiments, a plurality of laser sources is used.

The current and resistance sensor provided in the present invention is advantageous at least in that:

1. The device does not require the insertion of a dialysis membrane, improving the signal-to-noise ratio.
2. The assembling procedures are simplified, resulting in fewer operational errors.
3. Each chamber of the device can be accessed independently. The solution in the sample chamber does not require the same buffered condition as in the photo-induced-voltage-generating solution chamber.
4. More than one chamber can be set up to test multiple samples at the same time.

BRIEF DESCRIPTION OF THE SEVERAL VIEWS OF THE DRAWINGS

Embodiments of the technology of the present invention are described by way of example only, with reference to the accompanying drawings, wherein:

FIG. 1 illustrates a schematic diagram of the conventional current and resistance sensor.

FIG. 2 illustrates a schematic diagram of the current and resistance sensor of an embodiment of the present invention.

FIG. 3 illustrates the photo-induced current of a cell-based or protein-based of an embodiment of the present invention.

FIG. 4A to 4B illustrate schematic diagrams of the current and resistance sensor of an embodiment of the present invention.

FIG. 5 illustrates a schematic diagram of a current and resistance sensor of an embodiment of the present invention.

FIG. 6 illustrates a schematic diagram of a current and resistance sensor of an embodiment of the present invention.

FIG. 7 illustrates a schematic diagram of a current and resistance sensor of an embodiment of the present invention.

FIG. 8A to 8B illustrate schematic diagrams of a current and resistance sensor of an embodiment of the present invention.

FIG. 9 illustrates the photo-induced current diagram of microbial rhodopsin of an embodiment of the present invention.

FIG. 10 illustrates the effect of different concentrations of sodium chloride solution on the conductivity and photo-induced current of an embodiment of the present invention.

FIG. 11 illustrates the effect of laser light source on the photo-induced current of different bacteriorhodopsin in an embodiment of this invention.

FIG. 12 illustrates a test of the average value of the continuous photo-induced current of an embodiment of the present invention.

FIG. 13 illustrates the effect of different concentrations of salt solutions on the photo-induced current of an embodiment of the present invention.

FIG. 14 illustrates the effect of different laser intensities and different bacteriorhodopsin concentrations on the photo-induced current of an embodiment of the invention.

FIG. 15 illustrates the effect of different laser positions on the photo-induced current of an embodiment of the present invention.

FIG. 16 illustrates the effect of different chamber lengths on the photo-induced current of an embodiment of the present invention.

FIG. 17 illustrates the effect of different loading volumes on the photo-induced current of an embodiment of the present invention FIG. 18 illustrates the effect of different protein concentrations on the photo-induced current of an embodiment of the present invention.

FIG. 19 illustrates the effect of different proteins on photo-induced current at different salt solution concentrations in an embodiment of the present invention.

FIG. 20 illustrates the electrophoresis and spectra of Lucifer yellow-labeled proteins of an embodiment of the present invention.

FIG. 21 illustrates the effect of Lucifer yellow-labeled proteins on photo-induced current at different salt solution concentrations in an embodiment of the present invention.

FIG. 22 illustrates the effect of Gα subunit before and after activation on photo-induced current of an embodiment of the present invention.

FIG. 23 illustrates the effect of suppression of Gα subunit on photo-induced current in an embodiment of the present invention.

FIG. 24 illustrates the GTPγS saturation binding analysis of AtGPA1 in an embodiment of the present invention.

FIG. 25A to 25C illustrate continuous and steady-state photo-induced current of different microbial rhodopsin cell-based of an embodiment of the present invention.

FIG. 26 illustrates the photo-induced current signal of a current and resistance sensor in the form of a Wheatstone bridge of an embodiment of the present invention.

FIG. 27 illustrates the photo-induced current signal of a current-resistance sensor in the form of a Wheatstone bridge with different salt and protein concentrations in an embodiment of the present invention.

It is to be understood that aspects of the present invention are not limited to the configuration, means and characteristics shown in the accompanying drawings.

DETAILED DESCRIPTION OF THE INVENTION

As is conventional, the various features and elements in the drawings are not necessarily drawn to scale; the drawings are provided to show the features and elements related to the present invention in an ideal manner. In addition, identical or similar reference numerals in the drawings refer to similar elements or parts.

The following embodiments should not be regarded as unduly limiting the present invention. The embodiments discussed herein may be modified and varied by those having ordinary knowledge in the art to which the invention belongs without departing from the spirit or scope of the invention, and still fall within the scope of the invention.

As used herein, unless otherwise stated in the context, the terms "comprises," "includes," "has," or "contains" are inclusive or open-ended and do not exclude other unexplained elements or method steps; the terms "one" and "the" may be construed as singular or plural; the term "one or more" means "at least one" and thus may include a single feature or a mixture/combination. In addition, in the scope of the specification and the attached patent application, unless otherwise stated, "set on something" may be regarded as direct or indirect contact with the surface of something in the form of attachment or otherwise, and the definition of such surface shall be judged by the semantic meaning of the preceding and following paragraphs of the specification and the general knowledge of the field to which this specification belongs.

Single-Chamber Current and Resistance Sensor

Referring to FIG. 2(A), the present invention provides a current and resistance sensor 200A that includes: a photo-induced-voltage-generating solution chamber 220 for receiving a photoreceptor-protein-containing solution 230, and a compound layer 210 on one side of the photo-induced-voltage-generating solution chamber 220. The compound layer 210 is responsive to changes in the amount of protons in the solution 230. The compound layer 210 is provided with a gap 211 corresponding in position to the photo-induced-voltage-generating solution chamber 220 and is thus rendered discontinuous within the photo-induced-voltage-generating solution chamber 220.

As used herein, the term "photoreceptor protein" refers to a photosensitive protein involved in the reactions in an organism that are responsible for receiving and responding to optical signals, such as the rhodopsin in the photoreceptor cells of the retinae of vertebrates, the phytochromes in plants, and the bacteriorhodopsins and bacteriophytochromes in bacteria. The photoreceptor protein in the present invention is preferably a bacteriorhodopsin (BR), wherein the bacteriorhodopsin may include any rhodopsin in which the protons can be controlled with light. Bacteriorhodopsin is a light-driven transmembrane outward proton pump. Absorption of light at a specific wavelength (usually around 550 nm) causes a conformational change in the protein and alters the affinity between the proton and the proton-binding residue, resulting in proton release. A proton will be released from bacteriorhodopsin to the environment within 50 μs, followed by a proton uptake from the environment within 10 ms to restore the protein for another light activation. The whole process is termed a photocycle. The photocycle is subdivided into six intermediate states, beginning from the ground state and followed by the K, L, M, N, and O state. Each state is distinguishable from the unique characteristic absorption wavelength and represents the different stages of proton translocation in bacteriorhodopsin. The ground state ($\lambda$=550 nm), M state ($\lambda$=410 nm) and O state ($\lambda$=640 nm) can be measured from the time-resolved full spectrum analysis. The bacteriorhodopsin pumps out a proton before the M state and uptakes a proton between the M state and O state.

In a preferred embodiment, the bacteriorhodopsin is derived from *Haloarcula marismortui, Halobacterium salinarum* or *Haloquadratum walsbyi*, such as but not limited to *Haloarcula marismortui* bacteriorhodopsin I (HmBRI), *Haloarcula marismortui* bacteriorhodopsin II (HmBRII), *Halobacterium salinarum* bacteriorhodopsin (HsBR), *Haloquadratum walsbyi* bacteriorhodopsin (HwBR). Wherein, the above-mentioned bacteriorhodopsins comprise wild type and mutant, such as but not limited to D94N-HmBRI mutant.

As used herein, the term "changes in the amount of protons" refers to the changes in the amount of protons in a solution between different time points, in particular the changes in the amount of protons during a process in which the photoreceptor protein in the solution has an initial exposure to light, releases protons because of a change in protein conformation caused by the initial exposure to light, absorbs protons from the environment to restore the original protein conformation, and then waits for the next photo-activation reaction to take place.

As used herein, the term "compound layer" refers to a compound layer that is responsive to changes in the amounts of protons. The compound layer is a coating formed by a compound of indium tin oxide (ITO), indium zinc oxide (IZO), indium tungsten oxide (IWO), or fluorine-doped tin oxide (FTO). Preferably, the compound layer is indium tin oxide.

As used herein, the term "gap" refers to a line cut into the surface of a compound layer by a physical or chemical method so as to divide the compound layer into two electrically isolated sides, such that no electrical conduction path exists between the two electrically independent sides.

The compound layer 210 is applied on a substrate, and the present invention has no limitation on the material of the substrate, includes but not limited to glass, ceramic, non-birefringence material, wherein the non-birefringence material may be cellulose triacetate (TAC), cyclic olefin copolymer (COC), polycarbonate (PC), or cyclic olefin polymer (COP). The invention imposes no limitation on the material of the photo-induced-voltage-generating solution chamber 220 either, provided that this material does not react with the photoreceptor-protein-containing solution 230 chemically. For example, but not limited to the photo-induced-voltage-generating solution chamber 220 may be made of acrylic, silicone, resin, or a combination of the foregoing. To make the sensor of the invention, the first step is to coat a surface of a substrate with the compound layer 210. The surface of the substrate that is coated with the compound layer 210 is then cut to form the gap 211, thereby forming a "discontinuous compound layer" that is electrically isolated into two ends. The cutting method may be chemical or physical, including but not limited to laser cutting and etching. After that, the photo-induced-voltage-generating solution chamber 220 is provided on the surface of the compound layer 210, overlying the discontinuous compound configuration, in such a way that the photo-induced-voltage-generating solution chamber 220 corresponds to the gap 211, and by doing so, the current and resistance sensor 200A of the invention is completed.

In a preferred embodiment, the gap 211 divides the compound layer 210 into two ends (or two sides, namely a side 210*a* of the compound layer 210 and another side 210*b* of the compound layer 210), and the two ends are connected to the positive and negative electrodes of a voltage or current signal detector (such as but not limited to a galvanometer or an oscilloscope) respectively.

In another preferred embodiment, the two ends of the compound layer 210 are electrically coupled to an amplifier and then electrically coupled to an oscilloscope. More specifically, once the current and resistance sensor 200A is completed, the two ends of the compound layer 210 are connected to an oscilloscope in order for the oscilloscope to show the voltage signals produced by the current and resistance sensor 200A. Or, the current and resistance sensor 200A may be electrically coupled first to an amplifier to amplify the voltage signals produced, and then to an oscilloscope in order for the oscilloscope to show the amplified voltage signals. In a more preferred embodiment, an oscilloscope and a laser source are connected to a central processing unit so that the central processing unit can detect photo-activation and collect the resulting signals at the same time.

Referring to FIG. 2(B), the current and resistance sensor 200A of the present invention uses the gap 211 in the compound layer 210 to render the compound layer 210 discontinuous. When the photoreceptor-protein-containing solution 230 on the side 210*a* of the compound layer 210 is exposed to light, the protons released from the photoreceptor protein cause an increase in electric potential on the side 210*a* of the compound layer 210 and thereby generate a photo-induced current E. Blocked by the gap 211, the photo-induced current E flows from the side 210*a* of the compound layer 210 through an external voltage signal detector to the side 210*b* of the compound layer 210. When reaching the gap 211 again, the photo-induced current E is carried by the photoreceptor-protein-containing solution 230 and returns to the side 210*a* of the compound layer 210; thus, circulation of the photo-induced current E takes place. In contrast to the prior art, in which two compound-layer-coated plates and a dialysis membrane are required for generating a circulating photo-induced current, the present invention uses only one compound layer with a gap to achieve circulation of a photo-induced current.

According to an embodiment of the present invention, the current and resistance sensor further includes a laser source irradiating the for photoreceptor-protein-containing solution so that when the photoreceptor protein is exposed to the laser light, a current will be generated according to the theory stated above, as a result of changes in the amount of protons. Referring to FIG. 3(A), the generation of a photo-induced current by the photoreceptor-protein-containing current and resistance sensor after exposure to light can be divided into four stages: (I) photo-activation, (II) equilibrium, (III) re-uptake after the light is off, and (IV) restoration to the baseline. More specifically, during the light-on trigger, the photoreceptor-protein pumps out protons and drives the surface potential of the compound layer to increase. The potential difference creates a current to flow through the electrode on both sides of the compound layer in the manner described above. The current signal shows a steep peak at 0 second. As increasing amount of photoreceptor-proteins enters the proton reuptake phase, the proton diffusion effect occurs and the potential difference between the two electrodes starts to reduce until it reaches the equilibrium condition. At this stage, the photocurrent falls back to baseline value of zero. When the laser light is turned off, the proton pumping ceases, but the reuptake of protons is still proceeding, resulting in a reverse photocurrent signal. Finally, all photoreceptor-proteins restore to the ground state, and the electrical signal returns to baseline value of zero.

Referring to FIG. 3(B), in addition to the above purified photoreceptor-protein, the present invention is also applicable to cell-based of *E. coli* that exhibit photoreceptor-protein. The signal pattern obtained from the utilized cells is called cell-based photocurrent; unlike the protein-based photocurrent, in the cell-based photocurrent, the replenishment of protons is provided by the cytoplasm. Therefore, the reverse photo-induced current signal is not observed when the lights are off.

Validation of Single-Chamber Current and Resistance Sensor

Reference is now made to FIG. 4A and FIG. 4B. Panel (A) of FIG. 4A shows the two single-chamber current and resistance sensors under test, the upper one being a gapless single-chamber current and resistance sensor 200B, and the lower one being a gapped single-chamber current and resistance sensor 200A. When a laser source L projected light to the gapless single-chamber current and resistance sensor 200B or to the gap 211 of the gapped single-chamber current and resistance sensor 200A, no photo-induced current was detected (see panel (B) of FIG. 4A), but when the laser source L projected light to one of the two sides into which the compound layer 210 of the gapped single-chamber current and resistance sensor 200A is divided by the gap 211 (see panel (A) of FIG. 4B), a photo-induced current E was detected (see panel (B) of FIG. 4B).

Validation of Multiple-Chamber Current and Resistance Sensor

Reference is now made to FIG. 5 for a double-chamber current and resistance sensor as an example of a multiple-chamber design. According to an embodiment of the present invention, the current and resistance sensor 200C is further provided with a sample chamber 240 on the compound layer 210, and the compound layer 210 is further provided with a gap 211 corresponding to the sample chamber 240 and is thus rendered discontinuous within the sample chamber 240.

Specifically, a user may create as many sample chambers as the samples to be tested. If a sample to be tested is an electrically conductive substance or solution, there is no need to add a photoreceptor protein into the corresponding sample chamber or expose the sample to laser light. Conversely, if a sample to be tested is not electrically conductive, it is necessary to add a photoreceptor protein into the corresponding sample chamber and expose the sample to laser light in order to generate a photo-induced current. As shown in FIG. 5(A), the multiple-chamber current and resistance sensor 200C according to this embodiment of the present invention includes the photo-induced-voltage-generating solution chamber 220 and the sample chamber 240. The to-be-tested solution 241 in the sample chamber 240 may be an electrically conductive solution and in that case does not have to be added with a photoreceptor-protein-containing solution or exposed to laser light; the laser source L only has to project light to one side of the compound layer 210 that is within the photo-induced-voltage-generating solution chamber 220, and the photoreceptor-protein-containing solution 230 in the photo-induced-voltage-generating solution chamber 220 will be activated to generate a photo-induced current E that circulates along the path indicated by the arrows in FIG. 5(A), thereby allowing the magnitude of the current in the test sample to be obtained (see FIG. 5(B)).

Variant of the Current and Resistance Sensor of the Present Invention

Referring to FIG. 6, the compound layer may have more than one gap so as to form different types of circuits, including but not limited to a Wheatstone bridge. A Wheatstone bridge is a circuit that allows an unknown resistance to be measured by balancing two legs of the bridge circuit. One major advantage of a Wheatstone bridge is that it enables high-precision measurement of a resistance to be measured. FIG. 6(A) shows the circuit of a Wheatstone bridge in which $R_x$ is the resistance to be measured while $R_1$, $R_2$, and $R_3$ are known resistances. Therefore, the photo-induced-voltage-generating solution chamber serves as an electromotive force source, and the circuit is connected to the oscilloscope as a galvanometer. At the point of balance, i.e., no current passes through the oscilloscope ($I_G=0$), both the voltage and the current between the two midpoints (B and D) are zero. Therefore, $I_1=I_2$, $I_3=I_x$, $V_B=V_D$, and the $R_x$ can be derived from equation According to an embodiment of the present invention, referring to FIG. 6(B), the current and resistance sensor 300 has the circuit design of a Wheatstone bridge. A total of four sample chambers 320*b* are provided, namely a first sample chamber ($R_1$), a second sample chamber ($R_2$), a third sample chamber ($R_3$), and a test sample chamber ($R_x$). The gaps in the compound layer 310 that correspond respectively to the first sample chamber ($R_1$) and the third sample chamber ($R_3$) are connected to form a first gap 311*a*, and the gaps in the compound layer 310 that correspond respectively to the second sample chamber ($R_2$) and the test sample chamber ($R_x$) are connected to form a second gap 311*b*. Moreover, a portion of the first gap 311*a* that lies between the first sample chamber ($R_1$) and the third sample chamber ($R_3$) is connected by a third gap 311*c* to a portion of the second gap 311*b* that lies between the second sample chamber ($R_2$) and the test sample chamber ($R_x$). In a preferred embodiment, the two portions of the compound layer 310 that are separated by, and hence located respectively on two opposite sides of, the third gap 311*c* are connected to the positive and negative electrodes of an oscilloscope respectively, and the compound layer 310 is further cut to form a gap 311*d* corresponding to the photo-induced-voltage-generating solution chamber 320*a*, such that the compound layer 310, the photo-induced-voltage-generating solution chamber 320*a*, and the four sample chambers 320*b* corresponding to the aforesaid "H-shaped" gaps constitute a Wheatstone bridge. To use the current and resistance sensor 300, laser light is projected into the photo-induced-voltage-generating solution chamber 320*a* to generate a current that flows around the gaps into the first sample chamber ($R_1$) and the third sample chamber ($R_3$), the resistances of the samples in both of which are known. Then, by referencing the measurement of a galvanometer (implemented by the oscilloscope connected to the portions of the compound layer 310 that are separated by, and hence located respectively on two opposite sides of, the third gap 311*c*), the resistance of the sample in the test sample chamber can be calculated from the three known resistances.

Referring to FIG. 7 for the current and resistance sensor 400 according to another embodiment of the present invention, the two ends of the compound layer 210 are connected to a pair of electrically conductive probes 420*a* and 420*b* respectively. The electrically conductive probes 420*a* and 420*b* connected respectively to the two ends of the compound layer 210 can be inserted into different to-be-tested solutions in order to obtain the corresponding current signals respectively. It is also feasible for the current and resistance sensor 400 to be connected to multiple pairs of electrically conductive probes (not shown) in order to carry out high-throughput screening.

If the to-be-tested solution is electrically conductive, the material of the electrically conductive probes 420*a* and 420*b* only has to be electrically conductive. If, however, the to-be-tested solution is a biological solution sample, which may be electrolyzed by metal probes, it is important that the material of the electrically conductive probes 420*a* and 420*b* does not react with the solution sample. In a preferred embodiment, the conductive probe is a coating formed by a compound of indium tin oxide (ITO), indium zinc oxide (IZO), indium tungsten oxide (IWO), or fluorine-doped tin oxide (FTO). In a more preferred embodiment, the conductive probe is made of glass and coated with indium tin oxide.

The current and resistance sensor according to an embodiment of the present invention further includes at least one reflective mirror provided between a laser source L and the photo-induced-voltage-generating solution chamber (or a sample chamber). In another embodiment of the invention, a plurality of laser sources is used, and each laser source may project light directly into a sample chamber or has its light reflected into a sample chamber by a reflective mirror. In a preferred embodiment as shown in FIG. 8A, the current and resistance sensor 500 includes one laser source L and a plurality of reflective mirrors 510. The laser source L projects light to the reflective mirrors 510, and the reflective mirrors 510 reflect the light of the laser source L into a plurality of sample chambers respectively. The current and resistance sensor 500 of the invention, therefore, can be used in high-throughput screening. For example, a plurality of to-be-tested samples are added to a 96-well plate along with at least one control, and a plurality of reflective mirrors are placed under the sample wells respectively so that the samples can be measured at the same time by projecting laser light to the reflective mirrors simultaneously.

In another preferred embodiment as shown in FIG. 8B, the current and resistance sensor includes a plurality of laser sources and a plurality of reflective mirrors. The different laser sources project light to the different reflective mirrors respectively in order for the light to be reflected into different sample chambers. As shown in FIG. 8B, the current and resistance sensor 600 includes two laser sources L1 and L2 and two reflective mirrors 610 and 611. The two different laser sources L1 and L2 project light to the two different reflective mirrors 610 and 611 respectively in order for each reflective mirror to reflect light into the corresponding sample chamber.

EMBODIMENTS

The following non-limiting embodiments of aspects of the present invention are provided primarily for the purpose of illustrating aspects of the present invention and the benefits thereof achieved.

Materials and Methods

1. Purification of Photoreceptor Protein

The HEBR (with C-ter 6×His-tag) gene from *Haloarcula marismortui* was ligated into pET-21d and expressed in *E. coli* C43(DE3). A single colony of transformed cells was inoculated in Luria-Bertani (LB) medium supplemented with 50 μg/mL of ampicillin (amp) and incubated at 37° C. overnight. To scale up, a 1:50 (v/v) dilution of overnight culture was subculture into fresh LB/amp broth at 37° C. When the $OD_{600}$ of the culture reached 0.4-0.6, 1 mM isopropyl β-D-1-thiogalactopyranoside (IPTG) and 5 μM all-trans retinal (ATR) were added for induction. Following subsequent incubation for 4-6 hours in the dark, the cells were centrifugated at 6,750×g for 10 min at 4° C. (Hitachi CR-21, R10A3). The cells were then resuspended in buffer A (50 mM Tris-HCl, 4 M NaCl, 10 mM BME and 0.1 mM PMSF, pH 7.8) and broken down by ultrasonic processing (Misonix S-4000). To separate the membrane fraction, whole cell-extract centrifugation was performed at 39,000×g for 10 min at 4° C. (Hitachi CR-21, R20A2). The supernatant was centrifuged at 238,000×g for 1 hour at 4° C. (Hitachi CP80WX, P70AT). The sediment was dissolved in buffer B (buffer A supplemented with 2% DDM) for at least 12 hours at 4° C., followed by centrifugation at 39,000×g for 45 min at 4° C. (Hitachi CR-21, R20A2) to separate the detergent-soluble fraction.

Solubilized proteins were purified by affinity purification using the $Ni^{2+}$-nitrilotriacetate (Ni-NTA) method. The detergent-soluble solution containing 20 mM imidazole was incubated with Ni-NTA agarose at 4° C. for 4-6 hours on an orbital shaker. The mixture was transferred to a chromatography column and washed with buffer C (buffer A with 0.02% DDM and 100 mM imidazole). The target proteins were eluted with buffer D (buffer A with 0.02% DDM and 250 mM imidazole). The purified proteins were concentrated and exchanged into buffer E (100 mM NaCl, pH 6) with a protein concentrator (Millipore, Amicon, cut-off size of 30 kDa) and stored at 4° C.

2. Microbial Rhodopsin(MRho)-Expressed Cell Sample Preparation

*E. coli* C43 (DE3) transformed with microbial rhodopsin was cultured in 2 mL LB/amp broth at 37° C. overnight and then sub-cultured to 100 mL LB/amp broth. The cell was induced and supplied with 1 mM IPTG and 5 μM ATR at $OD_{600}$ 0.4-0.6, followed by incubation at 37° C. for 4 hours. The culture was then pelletized and resuspended in the unbuffered solution twice. Finally, the whole-cell sample was adjusted to $OD_{600}$ 50 and pH 6 for cell-based photocurrent measurement.

3. Sodium Dodecyl Sulfate Polyacrylamide Gel Electrophoresis (Sds-Page)

15% separation gel (15% acrylamide, 0.1% SDS, 0.1% APS, 0.03% TEMED, 375 mM Tris-HCl) and overlaid 4% stacking gel (4% acrylamide, 0.1% SDS, 0.1% APS, 0.045% TEMED, 125 mM Tris-HCl) were prepared in gel casting apparatus. The proteins were mixed with a 2× sample buffer (8% SDS, 15% glycerol, 100 mM Tris, 2 mM EDTA, 160 mM DTT, 0.2 mg/mL bromophenol blue), boiled for 10 min to denature the sample. Then, the sample was cooled to room temperature and loaded onto the gel. The anode and cathode buffer tanks were filled with a running buffer (90 mM Tris, 80 mM boric acid, 2.5 mM EDTA-2Na). A constant voltage of 60 V was supplied by means of a power pack. The voltage was switched to 140 V after the tracking dye of the sample reached the bottom of the stacking gel. The voltage was switched off when the tracking dye reached the bottom of the separation gel. The gel was then soaked in the staining solution (Coomassie brilliant blue R-250, CBR) for about 20 min with 120 rpm. The gel containing the staining solution was poured off completely and soaked in destaining solution (20% methanol, 10% acetic acid). The gel was kept on a rotary shaker until protein bands were visualized clearly with a transparent background. The destained gel was scanned and recorded.

4. Lucifer Yellow Labeling

The regulator of G protein signaling (RGS) protein without β-Mercaptoethanol (BME) was used for Lucifer yellow (LY) labeling. The protein solutions were kept in ice for 30 min with 1 mM tris(2-carboxyethyl)phosphine (TCEP) to prevent nonspecific cysteine cross-linking. Protein solution and LY were mixed at a 1:5 molar ratio of RGS4box/LY and kept in ice for 2 hours. Excess LY was removed by replacing the protein sample buffer with buffer G without BME and GDP. The samples were further resolved by UV-Vis spectrum and SDS-PAGE analysis, and photographs were taken on an ultraviolet (UV) light box to reveal the labeled proteins.

5. Steady-State Photocurrent Measurement

For protein-based photocurrent measurement, the mRho were first adjusted to 1-10 mg/mL and added to the photo-induced-voltage-generating solution chamber of the single chamber format. For cell-based photocurrent measurement, mRho-expressed cells were loaded into the photo-induced-voltage-generating solution chamber. Controlled by a central control unit (Raspberry Pi 400), a 0.5-W 532-nm continuous laser beam with a duration of 850 ms was applied to stimulate mRho. The current and resistance sensor was connected to a signal amplifier (SR570, Stanford Research Systems) and oscilloscope (Teledyne LeCroy WaveSurfer 4000HD) for photocurrent recording. For each series of measurement, 64 sets of measurement were averaged and graphed by GraphPad Prism.

6. Continuous Photocurrent Measurement

The photo-induced-voltage-generating solution chamber was filled with 20 mg/mL HEBR solution in the dual chamber format. The sample to be tested was added to the sample chamber at a volume of 100-150 μL. The photo-induced-voltage-generating solution chamber was illuminated by a 10-Hz, 532-nm flash laser (Nd-YAG laser, 6 ns pulse, pump energy 21 J) via a central control unit (Raspberry Pi 400) to generate the alternating photocurrent. The data recording system was identical to steady-state photocurrent measurement. Each data was collected at a single trigger event. The laser was triggered at 0 s and stopped at 40 s with each 5 s pre-trigger and post-illumination. Then, the raw data were recorded in a .csv file and processed by the Python code. The processed data were exported to an excel file for further analysis.

7. UV-Vis Spectrum Analysis and Protein Concentration Calculation

The purified and concentrated proteins were diluted 100-fold for absorption spectra measurements (U1900, Hitachi, Japan). The OD280 values were used to calculate the protein concentration by equation (1). The pathlength was 1 cm and other parameters were computed by Expasy ProtParam tool (https://web.expasy.org/protparam/). All measurements were performed at 25° C.

$$[\text{Protein}] = \frac{\text{Absorbance at } \lambda_{280}}{\text{Extinction Coefficient} \times \text{Pathlength}} \times \text{MW} \times \text{Dilusion factor} \quad (1)$$

TABLE 11

Molecular weight and extinction coefficient of proteins.

| Protein | Molecular weight (kDa) | Extinction coefficient ($M^{-1}$ $cm^{-1}$) |
|---|---|---|
| HEBR | 26.9 | 68410 |
| $G\alpha_{i1}$ | 41.4 | 35879 |
| Chi6 | 40.4 | 36900 |
| AtGPA1 | 45.5 | 42860 |
| AtRGS1box (249-459) | 24.8 | 15930 |
| RGS4box (51-177) | 14.2 | 18450 |

8. Full Spectrum Analysis of Photocycle

Flash-induced absorption transients were monitored using a flash-photolysis system. The flash laser was an Nd-YAG laser (532 nm, 6 ns pulse, 40 mJ). The purified proteins were suspended in buffer F (50 mM MES, 4 M NaCl, and 0.02% DDM, pH 5.8) to 4 mg/mL, and the transient absorbance changes were recorded at wavelengths 400-750 nm. The time length of measurement for HEBR was 0-2 seconds, and HwBR was 0-10 ms. Each data point was averaged 3 times with an integration time of 30 μs. The red and blue colors represent the increase and decrease of the absorbance at the indicated wavelength and time of laser excitation. All the measurements were performed at 25° C.

9. Purification of Gα Subunit

Plasmids containing Gα subunit (pET21d-Chi6, NpT7-5/Gαi1, pET16b-AtGPA1 with N-ter 6×His-tag) or RGS box (pET21d-RGS4box, pET21d-AtRGS1box with C-ter 6×His-tag) sequence were transformed into *E. coli* BL21(DE3) for protein expression. A single colony was picked and cultured into an LB medium with 50 μg/mL amp. To scale up, 1:50 (v/v) dilution of overnight culture was subculture into LB/amp broth at 373) Until OD600 of culture reached 0.4-0.6, 25 μM IPTG was added and the incubation temperature was adjusted to 25° C. followed by incubating for another 16 hours.

For purification of Gα subunit protein, the induced cells were collected by 6,800×g centrifugation for 10 min and then the pellets were gently resuspended in 1:90 of a cell culture volume of buffer G (50 mM Tris, 50 mM NaCl, 2 mM $MgCl_2$, 50 μM GDP, 10 mM BME, 0.1 mM PMSF, pH 8.0). The cells were disrupted by ultrasonication, and the total pulse time was set for 4 min: pulse-on for 5 s and pulse-off for 5 s with 55 watts power. The cell debris and inclusion bodies were removed by centrifugation at 39,000×g for 10 min and the supernatant was subsequently ultracentrifugated at 238,000×g for 1 hour to separate the soluble protein from the membrane fraction. The supernatant of ultracentrifugation was collected and mixed thoroughly with appropriate amounts of Ni-NTA resin with 20 mM imidazole in mild nutation at 4° C. for 1 hour. The mixture was transferred to a chromatography column and washed sequentially with two resin volumes of buffer H (buffer G with 20 mM imidazole) and buffer I (buffer G with 50 mM imidazole). The bound protein was eluted with buffer J (buffer G with 250 mM imidazole). Finally, the protein sample was concentrated and removed the imidazole by buffer exchanging with buffer G. For purification of the RGS box, the procedures were the same as purifying the Gα subunit but without 50 μM GDP in the buffer.

For anion exchange purification of Gα, the column (MonoQ) was first equilibrated with buffer G at a flow rate of 1 mL/min. A 250 μL volume of sample was then injected into the column, washed with 5-10 mL of Buffer G, and eluted with a NaCl gradient from 0 to 100% Buffer K (Buffer G and 1 M NaCl). The fractions contained target protein were collected and buffer exchanging with buffer G. The purified protein was aliquoted and stored in −80° C. for several months with no loss of function. All sample and buffers were filtered using 0.2-μm filters and degassed before used.

10. Functional Assay of Gα: $AlF4^-$ and GTPγS Dependent Activation

The intrinsic tryptophan in the switch-II region serves as a fluorescent probe for examining the activity of Gα subunit. In the $AlF_4^-$ dependent activation assay, the $AlF_4^-$ bound to GDP mimics the transition state of GTP hydrolysis, stimulating the conformational change of the switch-II region and enhancing the fluorescence quantum yields of intrinsic Trp. This principle was also applied to GDP/GTP auto-exchange, but it was conducted using of GTPγS, a non-hydrolyzable GTP analog. In the time-course of Trp fluorescence measurement, the excitation and emission wavelengths were 280 and 340 nm, respectively, and both slits are 10 nm. For $AlF_4^-$ dependent activation assay, 20 μL 20 μM Gα protein was first added into a cuvette filled with 1.5 mL buffer G without BME and PMSF at 50 s. Then 40 μL 500 mM NaF and 20 μL 10 mM $AlCl_3$ were added simultaneously at 100 s. For GDP/GTP auto-exchange, the experiments were conducted as described above using 1 μM GTPγS instead of $AlF_4^-$.

Result

1. Functional Testing of the Current and Resistance Sensor

First, the question of whether the present invention produces the photocurrent signal on the same principle as the conventional one needs to be confirmed. Therefore, a single chamber format device was tested with a highly expressible mutant, D94N-HmBRI (HEBR).

Referring to FIG. 9, a batch of *E. coli* cells expressing HEBR or the purified HEBR protein were prepared and individually added to the photo-induced-voltage-generating solution chamber. A steady-state photocurrent signal was recorded for both samples after being illuminated with a 532-nm continuous wave (CW) laser for an 850-ms period. Then, the same procedures were repeated with other bacteriorhodopsin and NpHR-expressed *E. coli* whole-cells (FIG. 9(A)) and the purified proteins (FIG. 9(B)). The light-on and light-off signals were observed. The signal patterns recorded from the single chamber device are comparable to those recorded from the conventional device.

2. Test of Photo-Induced Current Signal of Dual Chamber Format

The next question is whether the photocurrent signal can be measured by the two independent chambers aligned in the same circuit. Referring to FIG. 10, the HEBR was added to the photo-induced-voltage-generating solution chamber to serve as a voltage generator, while the sample chamber was filled with different concentrations of NaCl solution. Conductivity shows linearity for NaCl concentrations from 0.1 mM to 1 M (FIG. 10(A)), $R^2$=0.99). A linear increase in photocurrent (FIG. 10(B)), $R^2$=0.89) was also measured at higher log concentrations of NaCl in the sample chamber. The result shows that the photocurrent intensity is dependent on the conductivity of the solution in the sample chamber.

3. Continuous Photo-Induced Current Measurement

The results above showed that a dual chamber setup can be applied to measure the electrical resistance in the sample chamber. To serve as a real-time monitor of electric conductivity changes in the sample chamber, the photo-induced-voltage-generating solution chamber is required to function as an alternating current-like (AC-like) power supply. Therefore, the CW green laser in the setup above was replaced with a flash laser with a repetition rate of 10 Hz. Referring to FIG. 11, the flash laser serves as the light source to drive the photo-induced-voltage-generating solution chamber filled with either HEBR (FIG. 11(A)) or another bacteriorhodopsin from *Haloquadratum walsbyi*, HwBR (FIG. 11(B)). A consistent nanoampere current was recorded in a single photo-induced-voltage-generating solution chamber setup filled with two different BR proteins.

Referring to FIG. 12, in order to measure the photo-induced current continuously, recording time was extended to 45 seconds. The photo-induced-voltage-generating solution chamber was first filled with HEBR (20 mg/mL), and the light triggering started from 0 to 40 seconds. This recorded current was reduced to baseline value when the flash laser was turned off at 40 seconds (FIG. 12(A)). The raw data was processed by Python codes. To obtain the peak value of each photo-induced current from the measurement, the data was analyzed by the scipy.signal function find_peaksfinds, searching for all local maxima by comparing 1,300 neighboring values (FIG. 12(B)). The data points were then smoothed using a Savitzky-Golay filter to improve the precision of the data without distorting the signal tendency. Here, a window length of 7 and a degree 2 polynomial as the filter parameters was used (FIG. 12(C)). The average peaks value before and after smoothing are 36.473 nA and 36.429 nA, respectively, and the difference is not significant; however, the standard deviation of the smoothed data is 1.45, which is significantly lower than the 2.25 of the unsmoothed data. Finally, a continuous line was drawn using all filtered data points (FIG. 12(D)). An average value of the photo-induced current in a certain time interval can be calculated. The approach generates a reliable voltage source with less than 5% variation to detect the nanoampere-level current change.

4. Electrical Conductivity Test

Referring to FIG. 13, the dual chamber setup was tested to measure resistance of different solutions. The photo-induced-voltage-generating solution chamber was filled with HEBR, and the current was recorded with the sample chamber filled with 100 μL of four different salt solutions (NaCl, KCl, $CaCl_2$, and $MgCl_2$) from 1 to 100 mM. Results show the device of the present invention is capable of detecting the voltage continuously generated by the photo-induced-voltage-generating solution chamber when illuminated with 10-Hz flash 532-nm laser, and different electric conductivity solutions in the sample chamber resulted in different measured currents. All the salt solutions showed good linearity ($R^2$>0.99) in a concentration range from 1 to 100 mM.

5. Physical Parameters in the Photo-Induced-Voltage-Generating Solution Chamber

Referring to FIG. 14, there are several physical parameters that can affect the photocurrent results. First, different laser intensities and BR concentrations were tested in the photo-induced-voltage-generating solution chamber. The results show that the laser intensity (FIG. 14(A), $R^2$=0.97) and BR concentration (FIG. 14(B), $R^2$=0.95) are correlated to the photocurrent intensity. Furthermore, the dose-dependent results strongly demonstrate that the photocurrent induced by the flash laser is produced from the BR.

Second, referring to FIG. 15, different light positions can lead to the change of current direction. The direction of an electric current is directed away from the positive terminal and toward the negative terminal of the voltage source. Thus, three different light positions were examined, including the anode side (FIG. 15(A), position A), break region (FIG. 15(A), position B), and cathode side (FIG. 15(A), position C). Position A is default position of the laser illumination in the photo-induced-voltage-generating solution chamber. Switching the laser to position C, a reversed signal with equivalent intensity was measured, and no signal was detected at position B (FIG. 15(B)). From these results, the light position determines the positive terminal by activating the BR in that region.

6. Physical Parameters in the Sample Chamber

In the solution-based chamber, the photocurrent is conducted through the solution filled in the chamber. Thus, different loading volumes and the area of the solution-ITO interface may affect the conductivity and the measured current. To investigate the effect of these factors, tests on various loading volumes and chamber lengths were performed at both the sample chamber and photo-induced-voltage-generating solution chamber.

First, we modified the original chamber length of 15 mm into 10 mm and 5 mm, and the loading volumes decreased from 150 μL to 100 μL and 50 μL, respectively, to maintain the same solution depth. Referring to FIG. 16, adjusting the length of sample chamber results in a smaller area of the solution-ITO interface and thus lowers the conductivity of sample chamber (FIG. 16(A)). However, an opposite trend was observed in the photo-induced-voltage-generating solution chamber (FIG. 16(B)). Since the beam size of the laser and the total number of activated BR are constant, an enhanced photocurrent signal could be explained by the reduced proton diffusion effect with a shorter chamber length. Based on the results, the combination of a 15-mm sample chamber and a 5-mm photo-induced-voltage-generating solution chamber is considered the optimal chamber length parameter.

Referring to FIG. 17, next, the sample chamber was filled with five different loading volumes from 100 μL to 200 μL and the photocurrent was measured. The current increases linearly with the loading volume ($R^2$=0.96), which is in accordance with the law of resistance that a larger cross-sectional area of the substance improves the conductivity. The result implies that the impact of additional solution volume on photocurrent measurement should be considered when subsequent samples are loaded.

7. Protein Conductivity

Since different numbers of ionic charges on the protein surface and the protein itself can provide different electrical resistances, a protein's overall charge and geometric properties can render a unique conductivity.

Referring to FIG. 18, the photo-induced current under different concentrations of bovine serum albumin (BSA) and lysozyme were first measured in the pure water. Different protein concentrations from 5 to 50 mg/mL were loaded in the sample chamber. Recorded photocurrent rises with an increasing protein concentration. The BSA concentration lower than 25 mg/mL is below the detection limit. Logarithm analysis shows a correlation between protein concentration and photocurrent for lysozyme ($R^2$=0.95) and BSA ($R^2$=0.96). The result indicates that macromolecules such as protein have similar conductive properties to ionic species.

8. Protein-Ion Interaction

Previous results show different concentrations of protein and salt are measurable in the present device. The conductivity changes when the protein is dissolved in a salt solution was then analyzed. Referring to FIG. 19, considering that the total charge of protein varies at different pH values, BSA (pI=5) (FIG. 19(A)) and lysozyme (pI=10) (FIG. 19(B)) over a pH range of 4 to 10 in 10 mM, 100 mM, and 1 M NaCl solution were loaded into the sample chamber for test.

Comparing the trend of photocurrent with protein concentration, protein samples dissolved in 10 mM NaCl show a positive correlation while 100 mM and 1 M NaCl appears to be negatively correlated. An explanation was proposed for this phenomenon. The solubility of proteins usually increases slightly in the presence of salt, referred to as "salting in." However, at high concentrations of salt, the solubility of the proteins drops sharply, and proteins can precipitate out, referred to as "salting out." The solubility of protein can affect the overall charge and thus the conductivity of the solution. Comparing the high solubility lysozyme with the less soluble BSA, we can notice a trend towards a positive correlation between photocurrent and protein concentration.

Changes in protein conductivity are significant in 10 mM NaCl solution. Protein is neutral at its pI and exhibits a higher charge away from its pI. The lysozyme and BSA has a pI of around 10 and 5, respectively. As a consequent, the correlation between photocurrent and protein concentration increases as higher solution pH was applied. Although the difference in both 100 mM and 1 M NaCl solution is not significant, similar trend between photocurrent and protein concentration were also observed.

9. LY-Labeled Protein Test

In addition to adjusting solution pH, Lucifer yellow (LY) labeling is an alternative method to charge the protein artificially. LY is a Cys-directed fluorescent modifier with excitation-emission (Ex/Em) wavelengths of 428/536 nm. The protein with LY labeled can acquire two additional negative charges, resulting in a higher conductivity. The regulator of G protein signaling 4 (RGS4) protein can be labeled with LY at four cysteine residues, including $Cys^{71}$, $Cys^{95}$, $Cys^{132}$, $Cys^{148}$. Therefore, referring to FIG. 20, the RGS4 protein was first labeled with an LY probe and examined the labeling efficiency by SDS-PAGE (UV excitation and CBR staining) and UV-Vis spectroscopy (FIG. 20(A)). In the CBR staining result, the LY-labeled protein shifted into a larger molecular weight compared to the wild-type. Only the shifted band produced an emission signal when illuminated with the UV light. Additionally, an absorption peak at 428 nm was observed in the LY-labeled sample (FIG. 20(B)).

Next, referring to FIG. 21, wild-type RGS (R4) and LY-labeled RGS (R4-LY) were replaced with 10 mM or 100 mM NaCl solution, and loaded into the sample chamber for photocurrent measurement. The results showed that the photocurrent of the 10 mM NaCl solution followed a positive trend with increasing R4-LY concentration (FIG. 21(A)), suggesting that additional charges on the protein could be measured. However, there was no significant difference for the 100 mM NaCl solution group (FIG. 21(B)) which coincided with the result in protein-ion interaction analysis.

10. Protein-Ligand Interaction Measurement

Comprehensive investigation of physical properties has confirmed that the present device can measure the sample resistance. To further evaluate the performance of the present device, the nucleotide-binding protein Gα subunit is employed as a protein-ligand interaction model.

10-1. $AlF_4^-$ dependent activation of Gα

The Gα subunit is one of three G protein subunits that associate with G protein-coupled receptors (GPCRs) and contribute to transmembrane signaling. The Gα subunit binds to GDP as a ligand in its ground state and is exchanged from GDP to GTP when Gα is activated.

Previous studies have shown that the Gα subunit can interact with $AlF_4^-$, a complex compound of $AlCl_3$ and NaF. $AlF_4^-$ can enter the guanine nucleotide-binding pocket of the Gα subunit to imitate the gamma phosphate group of GTP. This transition state-mimetic form induces a conformational change, especially at helix II of the catalytic domain, which rotates nearly 100 degrees and changes the solvent accessibility of residues. On helix II of Gα, an intrinsically fluorescent probe, Trp211, can be used to confirm protein activity by providing a 280 nm excitation light and measuring emission changes at 340 nm.

Since the Gα subunit can interact with $AlF_4^-$ and affect the concentration of $AlCl_3$ and NaF, the conductivity may differ when the Gα subunit, $AlCl_3$, and NaF are added together. First, the human Gα subunit $G\alpha_{i1}$ and $G\alpha_t/G\alpha_{i1}$ chimera Chi6 were purified using $Ni^{2+}$ affinity and anion-exchange column. Purity was analyzed by SDS-PAGE, and activity was confirmed by fluorescence spectroscopy. Next, only $AlCl_3$ and NaF were added to the sample chamber for photocurrent measurement and an increase of current was observed (FIG. 22). When the Gα subunit was mixed with $AlCl_3$ and NaF, the current decreased significantly from 0.2 to 20 μM in a dose-dependent manner.

10-2. Inhibition of Gα Activation

Referring to FIG. 23, for the negative control, the Gα activation was inhibited by adding the EDTA to the solution. EDTA is a Gα subunit inhibitor that chelates $Mg^{2+}$ ions at the guanine-nucleotide binding site. $Mg^{2+}$ ions are essential to stabilize the binding force between $AlF_4^-$ and GDP in the Gα transition state. The effectiveness of Gα inactivation using EDTA was analyzed by fluorescence (FIG. 23(A)). The 20 μM Gα subunit in 10 mM EDTA has reduced activity by more than 60% and is almost inactivated at 100 mM EDTA. Photocurrent measurements with the inactivated Gα subunit showed no difference from the current added with $AlCl_3$ and NaF alone (FIG. 23(B)).

10-3. Kinetics of Gα Activation

After the successful measurement of the interaction of Gα with its ligand, the present device was extended to measure the $K_D$ of Gα and its ligands. In preliminary test, the plant *Arabidopsis thaliana* Gα AtGPA1 and a non-hydrolyzable GTP analog GTPγS were adopted. The substitution of sulfur for one of the oxygens in the γ-phosphate of GTP prevents the nucleotide from hydrolysis. Thus, the Gα with GTPγS can remain in an active state and facilitate the $K_D$ calculation. The reason to choose AtGPA1 rather than other mammalian Gα is because AtGPA1 is self-activating and has higher guanine nucleotide auto-exchange rate. Previous study has demonstrated that only AtGPA1 possessed the ability to bind GTPγS and release GDP without GPCR. The AtGPA1 was purified and analyzed the activity using the identical method in mammalian Gα purification.

Referring to FIG. 24, to calculate the $K_D$ of AtGPA1 and GTPγS, both photocurrent and fluorescence were measured. The data was converted into the percent of maximum to fit a hyperbola. According to the equation (2), $K_D$ is [P] when [L] is equal to [LP], the point at which half of the ligand binds to the substrate. In the experiment, $K_D$ is calculated around 1.5 nM. The estimation is close to the previous study reporting 0.8 nM derived from radioactive GTPγS assay. In conclusion, the present device is able to identify the protein-ligand interaction and analyze the kinetics of interaction.

$$K_D = \frac{k_{off}}{k_{on}} = \frac{[L][P]}{[LP]} \quad (2)$$

11. Whole-Cell Ion Pumping Measurement

The cell-based photocurrent with different types of rhodopsin expressed has been shown previously. The active transportation of ions across the cell membrane during light activation had been demonstrated to the *Halorhodopsin* (HR) and sodium-pumping rhodopsin (KR2). The translocation of ions between the inner and outer sides of the membrane alters the conductivity of the bacterial solution. Thus, the HR and KR2-expressed whole-cell were tested in the present device.

11-1. Dual Laser Controlling System

In an attempt to detect the changing signals from the present device, a dual laser controlling system was set up that could illuminate both the photo-induced-voltage-generating solution chamber and sample chamber at the same time. The bacterial cells can be loaded into the sample chamber for measurement. The microbial rhodopsins on the bacterial cell are activated during the laser illumination of the sample chamber. The laser-on signals were subtracted from laser-off signals to derive the relative photocurrent intensity of the test sample.

11-2. Ion Measurement of mRho-Expressed Cell

The bacterial cells expressed with KR2 (*Dokdonia eikasta*), NpHR and HEBR were suspended in 10 mM or 100 mM salt solution and loaded to the sample chamber. Different salt solutions (NaCl, KCl and $Na_2SO_4$) are used for testing the ionic species favored by proteins.

Referring to FIG. 25(A) to 25(C), for KR2-expressed cells (FIG. 25(A)), the cell-based steady-state photocurrent showed a downward signal in the groups with $Na^+$ (NaCl, $Na_2SO_4$). The same signal was not observed in group without $Na^+$ ($MgCl_2$). The $Na^+$ group had significantly higher photocurrent than the $Na^+$-free group in continuous photocurrent measurement. For NpHR-expressed cells (FIG. 25(B)), the whole-cell steady-state photocurrent showed a similar downward signal with KR2-expressed cells in groups of solutions provided with $Cl^-$ (NaCl, $MgCl_2$). This also, was not observed in the group without $Cl^-$ ($Na_2SO_4$). In continuous photocurrent measurement, the photocurrent was lower in $Cl^-$ group compared to the $Cl^-$-free group.

Unexpectedly, the photocurrent signal of the $Cl^-$-free group was not at the zero-baseline. However, the deviation from zero-baseline is less than 1 nA, which is within an acceptable range of variation. The control group of HEBR-expressed cells (FIG. 25(C)) showed an upward signal in the whole-cell steady-state photocurrent. The photocurrent is slightly higher in the continuous photocurrent measurement where the proton signal is more significant. The results suggest that the proton could also affect the measurement to a certain degree but is less significant than the effect of sodium ion. This assumption can be further confirmed by adding the CCCP (carbonyl cyanide m-chlorophenyl hydrazone), a reagent to facilitate the proton transport across the cell membrane, to investigate the impact of proton concentration on the measurement. Based on these results, the present device has the potential to detect the change in ion concentration or analyze the activity of ion-pumping proteins.

12. Wheatstone Bridge

To verify that the designed circuit is functioning as a Wheatstone bridge, the device was tested with different resistance of salt solutions in the sample chamber $R_x$. According to the Wheatstone bridge principle, if $R_x$ is equal to $R_2$, no current would be measured in the oscilloscope; if $R_x$ is not equal to $R_2$, a current signal would appear. Therefore, referring to FIG. 26, second chamber $R_2$ was first filled with 300 mM NaCl solution and then 3 mM or 300 mM NaCl solution was added into the sample chamber $R_x$. The results showed a 40-nA current when 3 mM NaCl was added (FIG. 26(A)) and no signal was detected when 300 mM NaCl was added (FIG. 26(B)). In addition, the positions of $R_2$ and $R_x$ were exchanged, and a reversed signal with equivalent intensity was measured (FIG. 26(C)). From these results, the designed circuit is confirmed to operate as a Wheatstone bridge.

Referring to FIG. 27(A), the Wheatstone bridge was tested with samples of different salt and protein concentrations. First, NaCl solution from 1 mM to 300 mM was added in the sample chamber Rr with 300 mM NaCl solution in chambers $R_1$ to $R_3$ for the photocurrent measurement. To interpret the result, the relationship between Rr and photocurrent was further analyzed. In FIG. 6(A), if the resistance of the galvanometer is high enough that $I_G$ is negligible, Rr can be computed from the three other resistor values and the supply voltage (Vs) (equation (3)). In the experiment, since the chambers $R_1$ to $R_3$ were loaded with the same 300 mM NaCl solution, the resistance values are identical and can be denoted as $R_1$. Thus, the equation (3) can be simplified as equation (4). From equation (4), the sample resistance Rr and photocurrent is a hyperbolic relationship, which is consistent with the experimental data (FIG. 27(A)). The range between 1 and 30 mM NaCl solution is approximately linear ($R^2$=0.88) and has the best sensitivity for detecting the slight change of resistance in the different samples.

$$V_G = \left(\frac{R_2}{R_1 + R_2} - \frac{R_x}{R_x + R_3}\right)V_S \quad (3)$$

$$V_G = \left(\frac{1}{2} - \frac{R_x}{R_x + R_1}\right)V_S \quad (4)$$

Next, referring to FIG. 27(B), following the same procedure as the previous experiment, protein (BSA or lysozyme) solution from 1 to 50 mg/mL was added in the sample chamber Rr. The results show dose linearity to the photocurrent intensity (FIG. 27(B)), which indicates that the protein charge difference can be measured from the Wheatstone bridge format. In conclusion, the current and resistance sensor in the form of a Wheatstone bridge has an advantage of measuring the resistance changes in low conductance solutions.

Based on the results above, the present device was then utilized to construct a resistivity-based device for protein interaction measurement. The BR behaves as an electric capacitor which can discharge at 50 us after laser activation. Taking advantage of the fast photocycle of BR, a continuous photocurrent was generated to measure the change in the resistance of the sample chamber in real-time. It was found that different numbers of ion charges result in different electric resistance, and the photocurrent is logarithmically proportional to the salt concentration. Notably, divalent ions were observed to show a higher conductivity than monovalent ions.

Furthermore, different protein samples were tested under the present device. Proteins with different resistivity showed distinct results. It was also discovered that different ionic strength provides different sensitivity to the protein charge measurement. In the experiments, the protein charge is positively related to the photocurrent at 10 mM NaCl solution, and is negatively related to the photocurrent at 100 mM and 1 M NaCl solution. Based on those results, the protein charge measurement has the best sensitivity at 10 mM NaCl solution.

The present device can also measure the ion pumping signal of microbial rhodopsins. It is demonstrated that the photocurrent before and after light activation of mRho-expressed *E. coli* has a significant difference. Similar to the protein interaction experiments, the present device has better sensitivity in 10 mM NaCl solution than in 100 mM NaCl solution. Unlike the conventional method that incorporated the mRho into a cell envelope vesicle and observed membrane potential, pH, and volume change, the present device provides a straightforward measurement of the ion pump activity directly.

The present device can be usefully employed in any kind of resistance measurement. Practically speaking, from materials, electronic components, chemicals, biomolecular modifications, conformational changes, or even interactions, etc., any changes in their forms, integrity, interactions, and chemical charges can lead to changes in resistance.

According to the above, the present invention provides an electrical-conductivity-based system for monitoring the interactions between biomolecules in real time. The system uses a stable microvolt-level voltage to detect a nanoamp-level current and thereby measure protein charges and the interactions between protein molecules. The invention provides a novel method for studying the behaviors of biomolecules without having to resort to surface modification. This method can serve as a prototype from which a system for high-throughput screening of biomolecule interactions can be constructed in the future.

All publications and patent applications cited in this specification are incorporated herein by reference, each of which is incorporated by reference, expressly in their respective entireties, for any purposes. In case of conflict between the specification and any publications or patent applications incorporated herein, the present specification will control.

While a detailed description of the present invention has been given above, it should be understood that the foregoing embodiments are only some preferred ones of the invention and are not intended to be restrictive of the scope of the invention. Any equivalent change or modification that is based on the appended claims shall fall within the scope of the invention.

What is claimed is:

1. A current and resistance sensor, comprising:

a photo-induced-voltage-generating solution chamber for receiving a photoreceptor-protein-containing solution; and a compound layer on one side of the photo-induced-voltage-generating solution chamber, wherein the compound layer is responsive to changes in the amount of protons in the solution, and the compound layer is provided with a gap that is an electrically insulating discontinuity aligned with and spanning the photo-induced-voltage-generating solution chamber, such that the compound layer is divided into electrically independent portions, and wherein changes in the amount of protons in the solution result in a detectable change in electrical current and/or resistance measured between the electrically independent portions across the gap.

2. The current and resistance sensor of claim 1, wherein the photoreceptor-protein is bacteriorhodopsin.

3. The current and resistance sensor of claim 2, wherein the bacteriorhodopsin is derived from *Haloarcula marismortui, Halobacterium salinarum* or *Haloquadratum walsbyi*.

4. The current and resistance sensor of claim 1, wherein the compound layer is divided by the gap into two ends, and the two ends are connected to a positive electrode and a negative electrode of an oscilloscope respectively.

5. The current and resistance sensor of claim 4, wherein the two ends of the compound layer are electrically coupled to an amplifier and then electrically coupled to the oscilloscope.

6. The current and resistance sensor of claim 1, wherein the compound layer is a coating formed by a compound of indium tin oxide (ITO), indium zinc oxide (IZO), indium tungsten oxide (IWO), or fluorine-doped tin oxide (FTO).

7. The current and resistance sensor of claim 1, further comprising at least one sample chamber provided on the compound layer, wherein the compound layer is further provided with a gap corresponding to each of the at least one sample chamber and is thus rendered discontinuous within each of the at least one sample chamber.

8. The current and resistance sensor of claim 7, wherein there are four said sample chambers, namely a first sample chamber ($R_1$), a second sample chamber ($R_2$), a third sample chamber ($R_3$), and a test sample chamber ($R_x$); the gaps in the compound layer that correspond respectively to the first sample chamber ($R_1$) and the third sample chamber ($R_3$) are connected to form a first gap; the gaps in the compound layer that correspond respectively to the second sample chamber ($R_2$) and the test sample chamber ($R_x$) are connected to form a second gap; and a portion of the first gap that lies between the first sample chamber ($R_1$) and the third sample chamber ($R_3$) and a portion of the second gap that lies between the second sample chamber ($R_2$) and the test sample chamber ($R_x$) are connected by a third gap.

9. The current and resistance sensor of claim 8, wherein the compound layer has two portions separated by, and hence located respectively on two opposite sides of, the third gap and connected respectively to a positive electrode and a negative electrode of an oscilloscope.

10. The current and resistance sensor of claim 1, wherein the compound layer is divided by the gap into two ends, and the two ends are connected to a pair of electrically conductive probes respectively.

11. The current and resistance sensor of claim 10, wherein the conductive probe is a coating formed by a compound of indium tin oxide (ITO), indium zinc oxide (IZO), indium tungsten oxide (IWO), or fluorine-doped tin oxide (FTO).

12. The current and resistance sensor of claim 1, further comprising a laser source.

13. The current and resistance sensor of claim 12, further comprising at least one reflective mirror provided between the laser source and the photo-induced-voltage-generating solution chamber or a sample chamber.

14. The current and resistance sensor of claim 12, wherein a plurality of laser sources is used.

* * * * *